(12) United States Patent
Nardi et al.

(10) Patent No.: US 7,618,384 B2
(45) Date of Patent: Nov. 17, 2009

(54) COMPRESSION DEVICE, SYSTEM AND METHOD OF USE

(75) Inventors: Steve Nardi, Taunton, MA (US); Jesse E Denson, Lincoln, RI (US); Scott Wudyka, Leominster, MA (US); Malcolm Bock, Medfield, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 24 days.

(21) Appl. No.: 11/533,524

(22) Filed: Sep. 20, 2006

(65) Prior Publication Data

US 2008/0071202 A1  Mar. 20, 2008

(51) Int. Cl.
*A61H 19/00* (2006.01)
*A61H 7/00* (2006.01)

(52) U.S. Cl. .................. 601/149; 601/97; 601/101; 601/103

(58) Field of Classification Search .............. 601/41, 601/44, DIG. 20, 104, 29, 101, 134, 107, 601/108, 27, 30, 31, 5, 133, 84, 97, 148–152, 601/143–145

See application file for complete search history.

(56) References Cited

U.S. PATENT DOCUMENTS

| | | | |
|---|---|---|---|
| 3,292,613 A | | 12/1966 | MacLeod |
| 3,396,721 A | | 8/1968 | Mencacci |
| 3,762,402 A | * | 10/1973 | Abramovitz ................. 601/65 |
| 3,826,249 A | | 7/1974 | Lee et al. |
| 3,862,629 A | | 1/1975 | Rotta |
| 3,892,229 A | | 7/1975 | Taylor et al. |
| 3,908,642 A | | 9/1975 | Vinmont |
| 3,971,398 A | | 7/1976 | Taylor et al. |
| 4,122,587 A | * | 10/1978 | Weiss et al. ..................... 5/621 |
| 4,153,050 A | | 5/1979 | Bishop et al. |
| 4,215,679 A | | 8/1980 | Rustin |
| 4,228,793 A | * | 10/1980 | Ramey ........................ 601/57 |
| 4,244,688 A | | 1/1981 | Kurz |
| 4,308,861 A | * | 1/1982 | Kelly ......................... 606/204 |
| 4,549,540 A | * | 10/1985 | Caspari et al. ............. 128/882 |
| 4,557,262 A | * | 12/1985 | Snow ......................... 606/201 |
| 4,702,235 A | | 10/1987 | Hong |
| 4,770,164 A | * | 9/1988 | Lach et al. .................... 601/41 |
| 4,795,148 A | | 1/1989 | Rangaswamy |
| 4,865,020 A | * | 9/1989 | Bullard ....................... 601/152 |
| 5,158,075 A | * | 10/1992 | Howard ....................... 601/79 |
| 5,295,996 A | * | 3/1994 | Blair .......................... 606/203 |
| 5,407,418 A | * | 4/1995 | Szpur ......................... 601/104 |

(Continued)

FOREIGN PATENT DOCUMENTS

AU  2002234848 B2  9/2002

(Continued)

*Primary Examiner*—Justine R Yu
*Assistant Examiner*—Annette F Dixon

(57) ABSTRACT

Apparatus and methods for cyclically compressing the limb of a patient to improve blood flow in the limb. In one embodiment, a compression device includes a compressive section sized and shaped for extending around a portion of the limb for applying compressive pressure and a housing operatively connected to the compressive section. The housing includes first and second housing members movable relative to each other between contracted and expanded positions. A non-pneumatic mechanical actuator is provided in the housing for cyclically moving the first and second housing members from their contracted position to their expanded position.

45 Claims, 17 Drawing Sheets

U.S. PATENT DOCUMENTS

| | | | |
|---|---|---|---|
| 5,743,864 A * | 4/1998 | Baldwin, II | 601/41 |
| 5,902,256 A * | 5/1999 | Benaron | 601/15 |
| 5,997,465 A | 12/1999 | Savage et al. | |
| 6,010,471 A | 1/2000 | Ben-Noon | |
| 6,179,797 B1 | 1/2001 | Brotz | |
| 6,224,538 B1 | 5/2001 | Wang et al. | |
| 6,290,662 B1 | 9/2001 | Morris et al. | |
| 6,423,017 B2 | 7/2002 | Brotz | |
| 6,582,449 B2 * | 6/2003 | Grey et al. | 606/204 |
| 6,620,116 B2 | 9/2003 | Lewis | |
| 6,676,613 B2 * | 1/2004 | Cantrell et al. | 601/41 |
| 6,736,785 B1 * | 5/2004 | Van Brunt | 601/44 |
| 6,757,916 B2 | 7/2004 | Mah et al. | |
| 6,960,159 B2 | 11/2005 | Chung et al. | |
| 6,984,201 B2 | 1/2006 | Khaghani et al. | |
| 7,226,427 B2 * | 6/2007 | Steen | 601/44 |
| 2003/0074711 A1 | 4/2003 | Iversen | |
| 2004/0073146 A1 | 4/2004 | Weintraub et al. | |
| 2004/0176709 A1 | 9/2004 | Van Brunt | |
| 2004/0260216 A1 * | 12/2004 | Zicherman | 601/111 |
| 2005/0015026 A1 | 1/2005 | Well et al. | |
| 2005/0148909 A1 * | 7/2005 | Weil et al. | 601/41 |
| 2005/0165333 A1 | 7/2005 | Rothman et al. | |
| 2005/0267387 A1 | 12/2005 | Baldauf et al. | |
| 2006/0009717 A1 | 1/2006 | Hall et al. | |
| 2006/0074362 A1 * | 4/2006 | Rousso et al. | 601/152 |
| 2006/0122546 A1 | 6/2006 | Rousso | |
| 2007/0055188 A1 | 3/2007 | Avni et al. | |
| 2007/0173886 A1 | 7/2007 | Rousso et al. | |
| 2007/0219474 A1 * | 9/2007 | Wen et al. | 601/49 |
| 2007/0299374 A1 * | 12/2007 | Gesotti et al. | 601/79 |
| 2008/0015630 A1 | 1/2008 | Rousso | |
| 2008/0039752 A1 | 2/2008 | Rousso | |

FOREIGN PATENT DOCUMENTS

| | | |
|---|---|---|
| IL | 141824 | 3/2001 |
| IL | 160185 | 2/2004 |
| IL | 160214 | 2/2004 |
| IL | 162373 | 6/2004 |
| IL | 164284 | 9/2004 |
| IL | 164285 | 9/2004 |
| IL | 164286 | 9/2004 |
| WO | 02069879 A1 | 9/2002 |
| WO | 2005051250 A1 | 6/2005 |
| WO | 2005072674 A1 | 8/2005 |
| WO | 2005074376 A2 | 8/2005 |
| WO | 2005120424 A2 | 12/2005 |
| WO | 2005120500 A2 | 12/2005 |
| WO | 2005122269 A2 | 12/2005 |
| WO | 2006033114 A2 | 3/2006 |
| WO | 2006033115 A2 | 3/2006 |
| WO | 2006040109 A1 | 4/2006 |
| WO | 2006117771 A1 | 11/2006 |
| WO | 2007/033401 A1 | 3/2007 |

* cited by examiner

COMPRESSION DEVICE, SYSTEM AND METHOD OF USE

BACKGROUND OF THE INVENTION

This invention relates generally to compression therapy, and more particularly to devices which enhance blood flow to avoid circulation problems, such as deep vein thrombosis (DVT).

Cyclical compression of a body part (e.g., leg) is beneficial to a person who has a blood circulation problem involving poor venous return to the heart. Many devices on the market and in the prior art provide compression by using one or more pneumatic bladders that encircle the leg or other limb(s). The bladders are inflated in a predetermined sequence and to a prescribed pressure at timed intervals. The device that controls the inflation typically employs an air pump or compressor and a number of valves that operate to direct the flow of air to the bladders. Conventional products use a bladder-filled sleeve wrapped around the limb and a tube that connects the bladder(s) to a controller device that resides separately from the patient such as on the footboard of a bed, on the floor, or on a night stand. If the patient must move, the device must be removed. In addition, while the device is on the patient, it is possible that tubes become entangled in the patient's limbs and/or become a nuisance or safety hazard to caregivers and visitors who may be close to the bed.

There is a need, therefore, for an improved compression device.

SUMMARY OF THE INVENTION

In general, a compression device of this invention is used for cyclically compressing the limb of a patient to improve blood flow in the limb. The compression device comprises a compressive section sized and shaped for extending generally circumferentially around a portion of the limb for applying compressive pressure to the limb portion, and a housing operatively connected to the compressive section. The housing includes first and second housing members movable relative to each other between a contracted position in which the housing has a first dimension for relaxing pressure on the limb portion, and an expanded position in which the housing has a second dimension greater than the first dimension for compressing the limb portion. A non-pneumatic mechanical actuator is provided in the housing for cyclically moving the first and second housing members from their contracted position to their expanded position.

In another aspect, this invention is directed to a compression system which includes at least two of the compression devices described above and, in addition, a single integrated control system for controlling the operation of the at least two compressive devices.

In still another aspect, this invention is directed to a method of using a compression device to cyclically compress the limb of a patient to improve blood flow in the limb. The compression device comprises a compressive section sized and shaped for extending generally circumferentially around a portion of the limb for applying compressive pressure to the limb portion, and a housing operatively connected to the compressive section. The housing includes first and second housing members movable relative to each other between a contracted position in which the housing has a first dimension and an expanded position in which the housing has a second dimension greater than the first dimension. The method comprises the steps of first applying the compression device to a limb of a patient such that the compressive section extends circumferentially around a portion of the limb, and then cyclically activating a non-pneumatic mechanical actuator located inside the housing to move the housing members from their contracted position to their expanded position in a series of cycles to cyclically compress the limb.

In another aspect, this invention is directed to a method of using a compression system to cyclically compress portions of a limb of a patient to improve blood flow in the limb. The compression system comprises a compressive unit having zones corresponding to different portions of a limb, and at least two modules each comprising a housing including first and second housing members movable relative to each other between a contracted position in which the housing has a first dimension and an expanded position in which the housing has a second dimension greater than the first dimension. The method comprises the steps of applying the compressive unit to a limb such that the compressive unit extends circumferentially around the limb and the zones of the unit correspond with the limb portions to be cyclically compressed, and operatively connecting the modules to the compressive unit such that the modules are positioned in respective zones of the compressive unit. The housing members are then caused to move cyclically between their expanded and retracted positions for cyclically compressing the limb portions.

In another aspect, a compression device of this invention comprises a compressive section sized and shaped for extending generally circumferentially around a portion of the limb for applying compressive pressure to the limb portion, and a module operatively connected to the compressive section for cyclic expansion and contraction in generally radial directions with respect to the limb portion between a contracted condition in which the module has a first dimension for relaxing pressure on the limb portion, and an expanded condition in which the module has a second dimension greater than the first dimension for compressing the limb portion. The module comprises the combination of at least one pneumatic bladder and at least one non-pneumatic mechanical device. The at least one non-pneumatic mechanical device is operable to apply a force in a generally radial direction with respect to the limb portion for moving the module toward its expanded condition.

In another aspect, this invention is directed to a disposable band for use in a compression therapy to improve blood flow in the limb of a patient. The band comprises a band member adapted to extend circumferentially around a portion of the limb. The band member has opposite ends. A fastening device is provided on the band member for releasable attachment of opposite ends of the band member to secure the band member around the limb portion. A pocket on the band member is sized and shaped for receiving a module cyclically movable between a contracted condition in which the module has a first dimension for relaxing pressure on the limb portion and an expanded position in which the module has a second dimension greater than the first dimension for compressing the limb portion. The module is removable from the pocket whereby on termination of the compression therapy the band can be disposed and the module re-used with a different disposable band.

Other objects and features will be in part apparent and in part pointed out hereinafter.

BRIEF DESCRIPTION OF THE DRAWING

Corresponding parts are indicated by corresponding reference numbers throughout the several views of the drawing.

DETAILED DESCRIPTION

Figure 1:
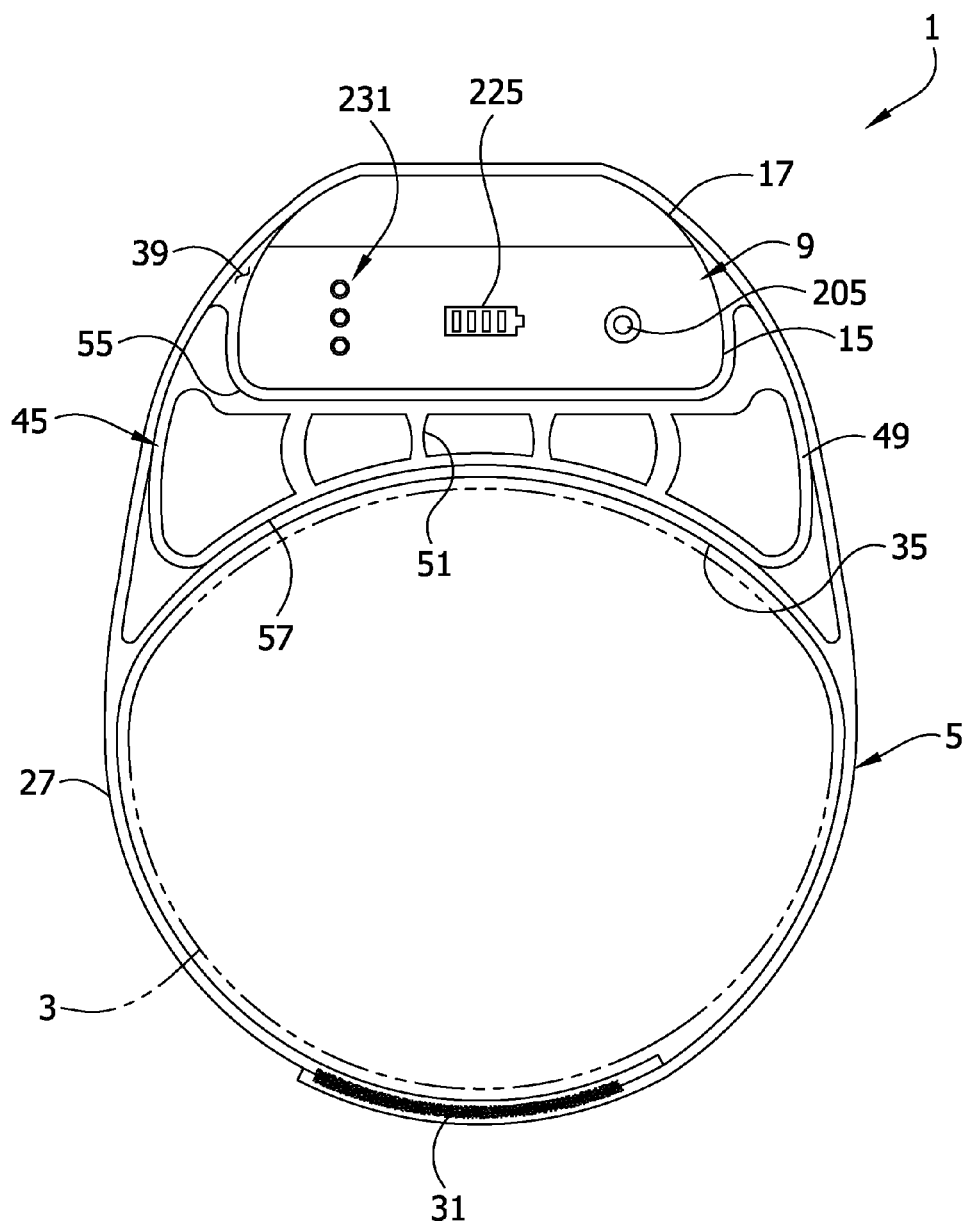
FIG. 1 is an elevational view of a compression device of this invention as applied to the limb of a patient (shown in phantom) and showing first and second housing members of the device in a contracted position.
Figure 2:
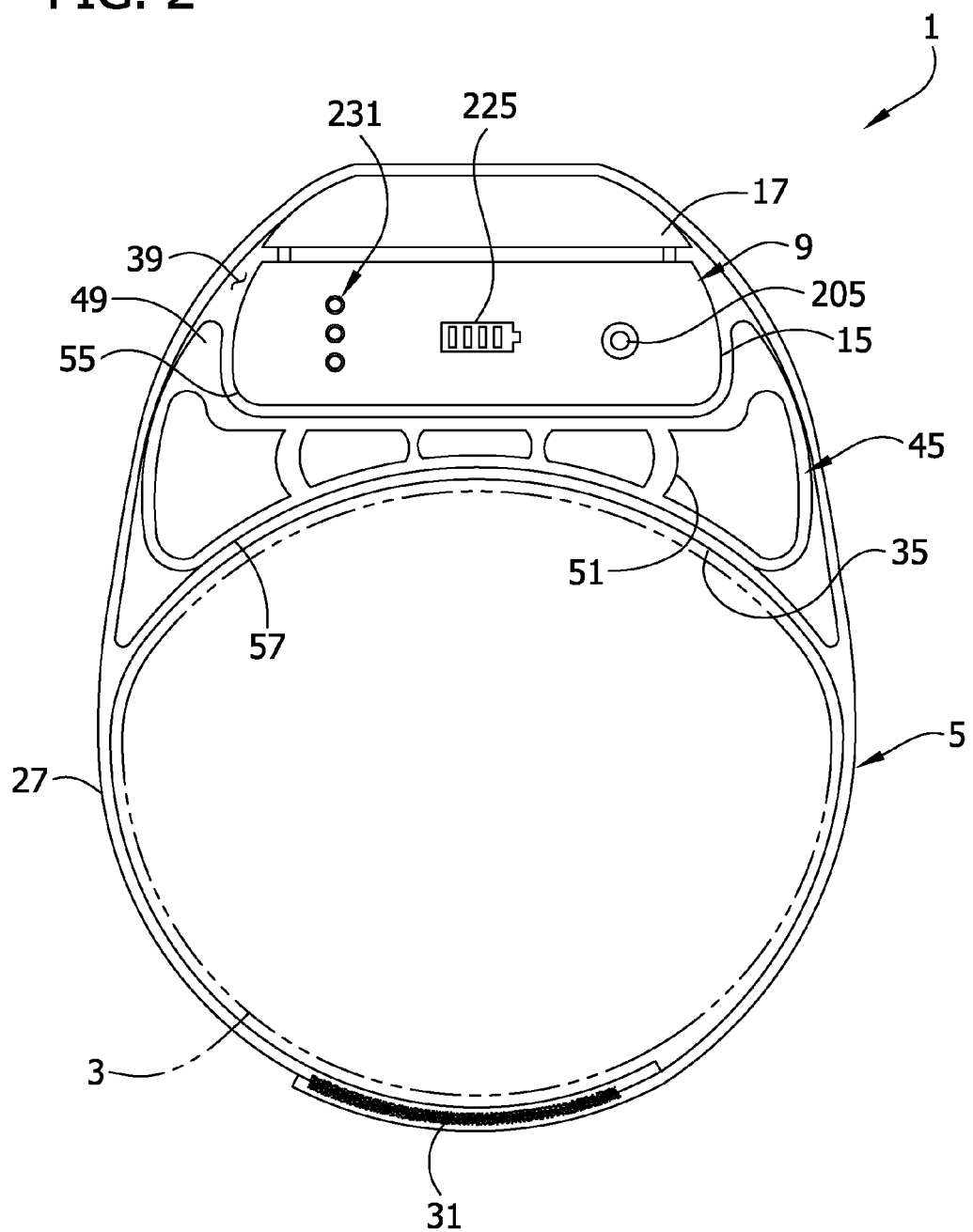
FIG. 2 is a view similar to FIG. 1 showing the housing members in an expanded position for compressing the limb.
Figure 3:
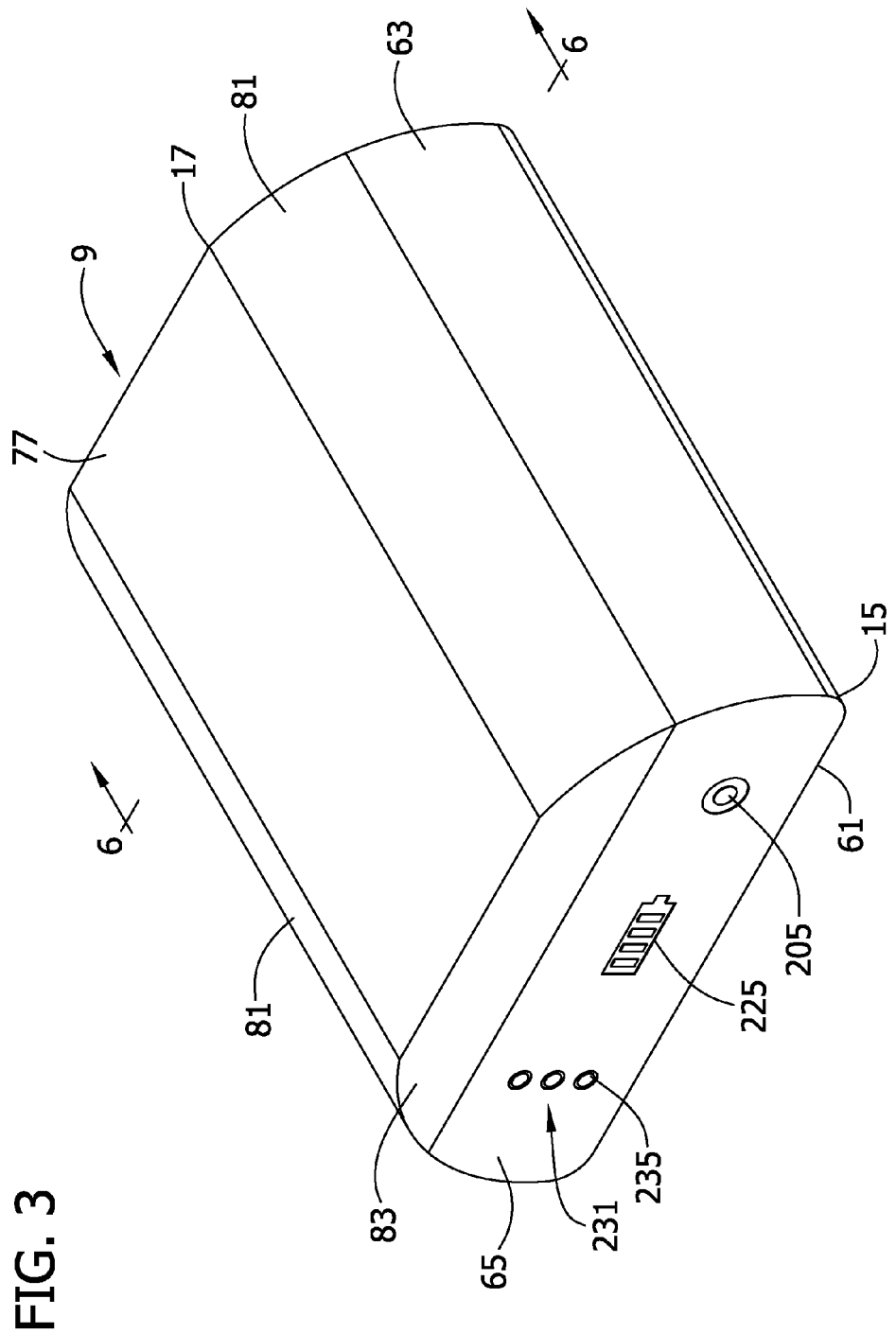
FIG. 3 is a perspective view of the housing in its contracted condition.
Figure 4:
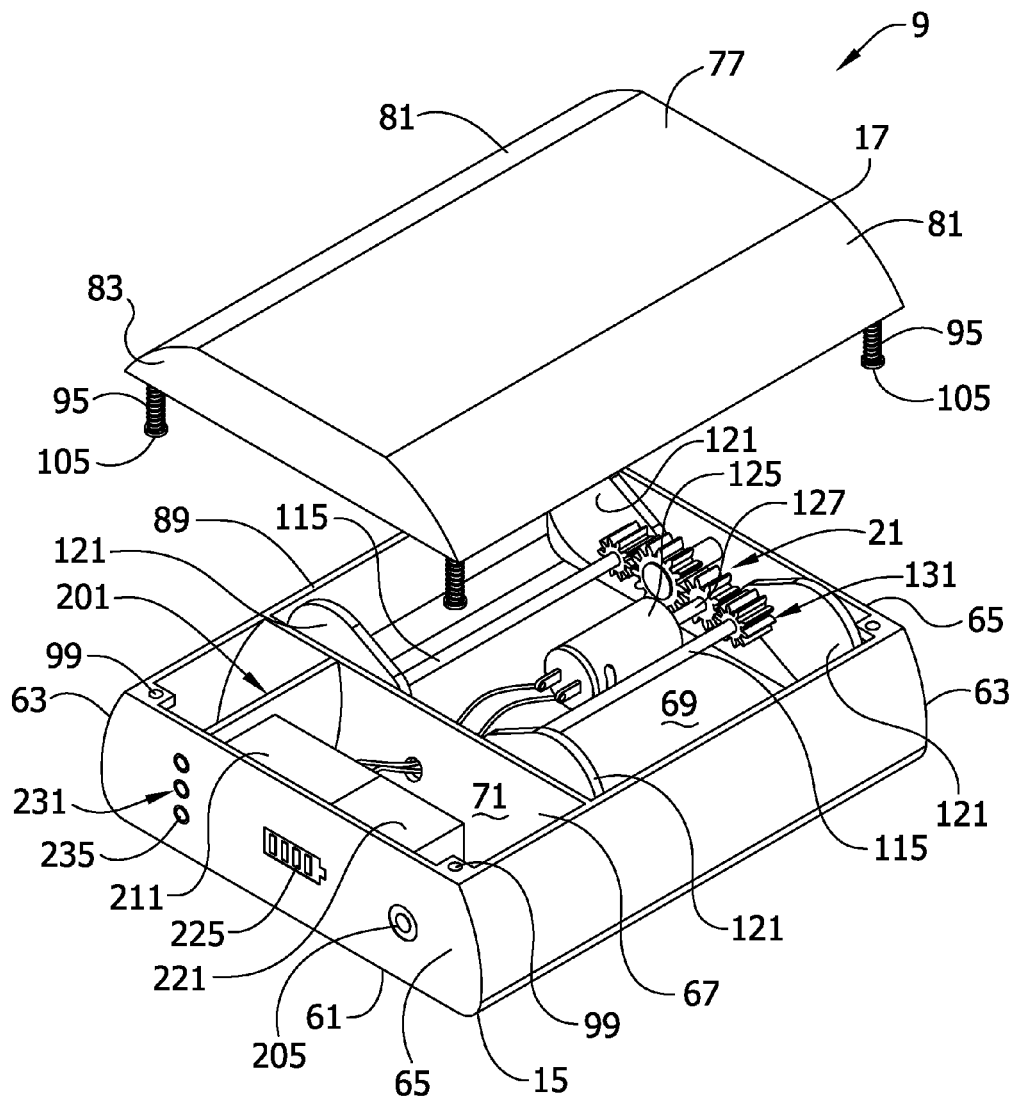
FIG. 4 is a view similar to FIG. 3 but with the housing members exploded to show an actuator inside the housing.
Figure 6:
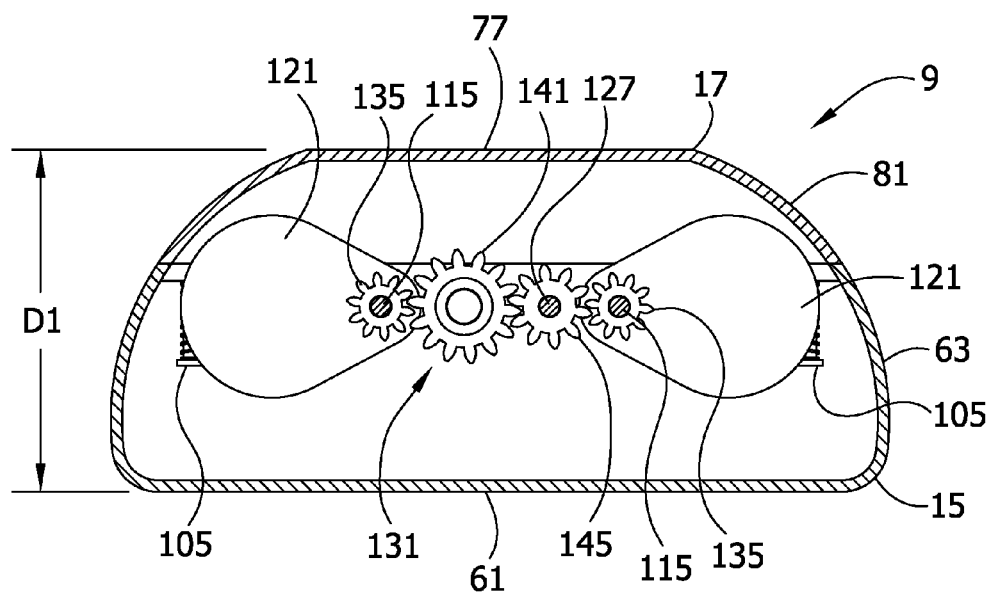
FIG. 6 is a schematic view of the actuator and the housing members in their contracted position.
Figure 7:
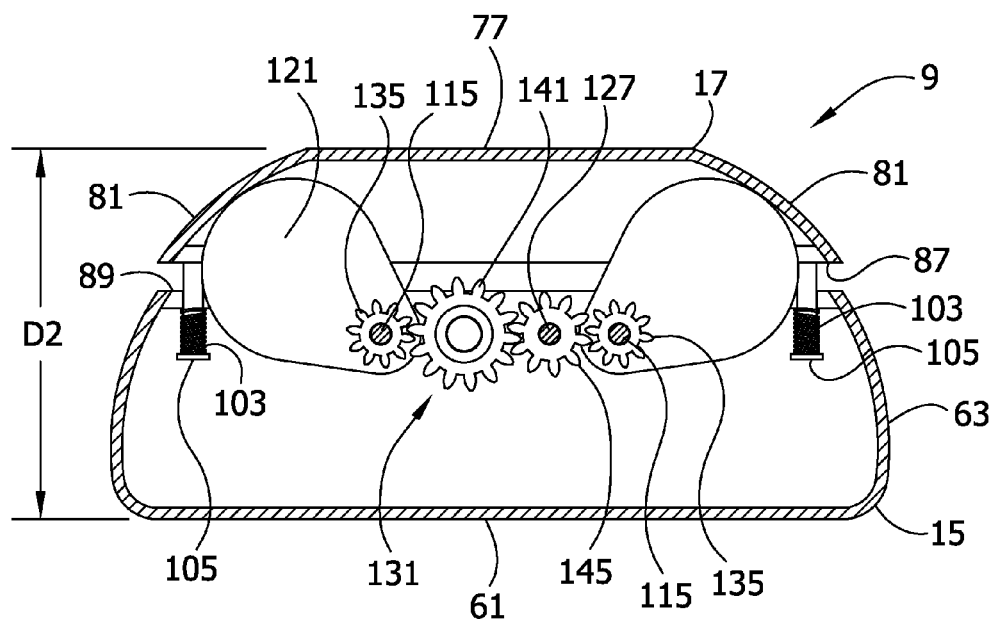
FIG. 7 is a view similar to FIG. 6 but showing the housing members in their expanded position.

Referring now to FIGS. 1-3, one embodiment of a compression device of this invention is designated in its entirety by the reference numeral 1. As will be explained in detail hereinafter, the device is used for cyclically compressing the limb of a patient to improve blood flow in the limb. By way of example, the limb may be a leg, foot or arm generically indicated at 3 in FIGS. 1 and 2. In general, the compression device comprises a compressive section, generally designated 5, sized and shaped for extending generally circumferentially around a portion of the limb 3 for applying compressive pressure to the limb portion, the limb and limb portion both being numbered 3 in the figures. The compression device 1 also includes a housing, generally designated 9, operatively connected to the compressive section 5. The housing 9 includes first and second housing members indicated at 15 and 17, respectively, movable relative to each other between a contracted position in which the housing has a first dimension D1 (FIG. 6) for relaxing pressure on the limb portion, and an expanded position in which the housing has a second dimension D2 (FIG. 7) greater than D1 for compressing the limb portion. An actuator, generally indicated at 21 in FIG. 4, is provided in the housing 9 for cyclically moving the first and second housing members between their contracted (FIG. 1) and expanded (FIG. 2) positions.

In one embodiment (see FIGS. 1 and 2), the compressive section 5 comprises a generally annular band 27 which encircles the limb 3. The band material is preferably soft and non-abrasive to the skin and may include a slipping, non-compliant material at the interface of the band and the patient. Desirably, the material is breathable and may have hydrophilic properties that help to improve patient comfort by creating a dry condition at the skin. (A dry skin condition tends to minimize chafing and abrasion, since the material is less likely to stick to the skin.) By way of example, the band 27 may be of a non-woven PVC material which is substantially non-stretchable. As shown in FIGS. 1 and 2 the band 27 comprises a band member (also designated 27) having opposite ends releasably secured together by means of a fastening device 31 (e.g., mating hooks and loops, releasable adhesives, snaps, buttons or other mechanisms) to provide circumferential adjustment to enable the band to fit limbs of different sizes. The band member 27 comprises a single elongate piece of material. Alternatively, the band member 27 can be formed in multiple pieces. For example, the band member 27 can comprise a first piece releasably attached to one side of the second housing member 17 and a second piece releasably attached to an opposite side of the second housing member 17. Also, the band member 27 can be of varying length and width to accommodate limbs of differing sizes and shapes. During use, one compression device 1 can have a thinner and shorter band member 27 to fit around the calf, while a second compression device can have a wider and longer band member 27 to fit around the thigh.

In the illustrated embodiment (FIGS. 1 and 2), the band 27 includes an interior layer 35 of material secured to the exterior layer of the band to form an interior pocket 39 which is sized and shaped for removably receiving the housing 9 containing the actuator 21. The pocket has at least one open end for insertion of the housing into the pocket. A releasable closure such as a closure flap (not shown) can be provided for closing the open end of the pocket 39 to secure the housing in the pocket until such time as access is needed or desired. The housing 9 may be releasably secured in place in the pocket 39 by other means or combinations of means. For example, in one embodiment, an attaching member (not shown) is secured to an inside surface of the pocket 39. The attaching member and housing 9 have mating detent components that securely, but releasably hold the housing in place. In another embodiment, mating hook and loop fasteners on the housing 9 and on an interior surface of the pocket 39 or pocket closure (if used) can be used to releasably secure the housing 9 in the pocket. In yet another embodiment, the housing 9 is snuggly fitted between semi-rigid holders secured within the pocket, creating a slip fit or interference fit. A release latch can be used to hold the housing 9 in place for additional sturdiness. After use of the compression device 1, the housing 9 may be removed from the pocket 39 for re-use with a different (fresh) band. Typically, the band 27 is discarded after a single use.

A force-distributing device (generally designated 45) is interposed between the housing 9 and the limb 3 for distributing compressive forces applied by the device 1 more evenly across the limb. As shown in FIGS. 1 and 2, this device 45 comprises a cushion 49 received in the pocket 39, the pocket being sized and shaped to hold both the housing 9 and the device 45 at a location between the housing 9 and the limb 3 of the patient. In the embodiment shown in FIGS. 1 and 2, the cushion 49 comprises an extruded body of soft resilient rubber-like material having open cells separated by flexible walls 51 which absorb the compressive forces and distribute them more uniformly over the limb 3. The cushion 49 has an upper surface 55 which conforms to the bottom (base member 15) of the housing 9 and which extends up on opposite sides of the housing to cradle it, and a lower surface 57 which is adapted to conform to the convex shape of a limb and which has rounded corner edges to minimize any pinching or abrasion of the skin. In another embodiment, the cushion 49 comprises a sealed bladder filled with air or other suitable gas. (Various bladder embodiments are described later in this specification.) In yet another embodiment (not shown), the cushion comprises a substantially solid body formed from a pliant gel-like material. Regardless of form, the force-distributing device 45 may be attached (e.g., adhered or otherwise fastened) to the housing 9, or it may be unattached to the housing.

In some embodiments, the compression device may be used without a force-distributing device (e.g., device 45). In these embodiments, the pocket 39 is preferably of a smaller size.

As illustrated in FIGS. 3, 4, 6 and 7, the first housing member 15 comprises a base member (also designated 15) having a bottom wall 61, opposite upstanding side walls 63 and opposite upstanding end walls 65. In the embodiment shown, the base member 15 is substantially rectangular, but other shapes can be used without departing from the scope of this invention. The interior space defined by the base member 15 is divided by a partition 67 into a first section or compartment 69 containing the actuator 21 and a second section or compartment 71 containing components for controlling the operation of the compression device (more on this later).

The second housing member 17 comprises a cover member (also designated 17) having a substantially planar top wall 77 generally parallel to the bottom wall 61 of the base member 15, opposite side walls 81 curving down from the top wall, and opposite end walls 83 extending down from the top wall. The top, side and end walls of the cover member 17 may have other shapes.

The base and cover housing members 15, 17 are fabricated from a suitable material, such as a flexible plastic or a rigid plastic having an outer coating of a more resilient material (e.g., an over-molded spongy or rubbery material). The parts may be molded as one-piece parts having a relatively thin-wall construction to reduce expense and weight.

The base and cover members 15, 17 of the housing are adapted to be moved by the actuator 21 from their stated contracted position to their stated expanded position. In a contracted position, the cover member 17 is spaced relatively close to the base member 15 and, in one embodiment, the bottom rim 87 of the cover member mates with the top rim 89 of the base member. In its contracted position (FIG. 6), the housing 9 has the aforesaid dimension D1 which is shown as representing the overall height of the housing in its contracted state. In expanded position (FIG. 7), the cover member 17 of the housing is spaced farther away from the base member 15 so that the housing has the aforesaid dimension D2 representing an increased overall height of the housing (FIG. 2). The specific way in which the housing members 15, 17 are arranged or fit together can vary without departing from the scope of this invention. For example, rather then having abutting rims 87, 89, the base and cover members 15, 17 may have side walls which telescope relative to one another to provide the necessary dimensional change.

Figure 5A:
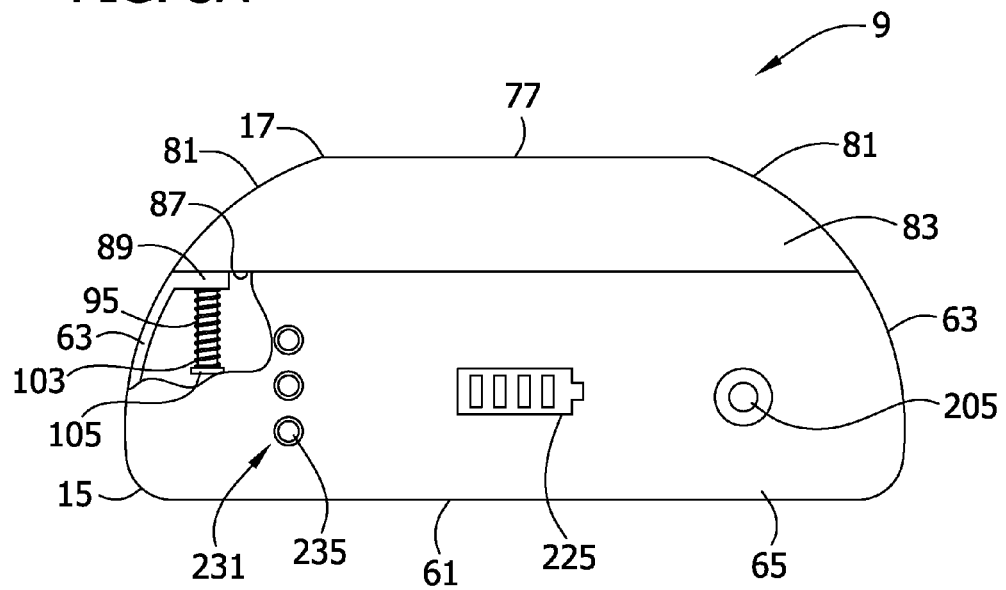
FIG. 5A is an end view of the housing in a contracted position with a portion of the side wall broken away to show a spring arrangement urging the housing toward its contracted condition.
Figure 5B:
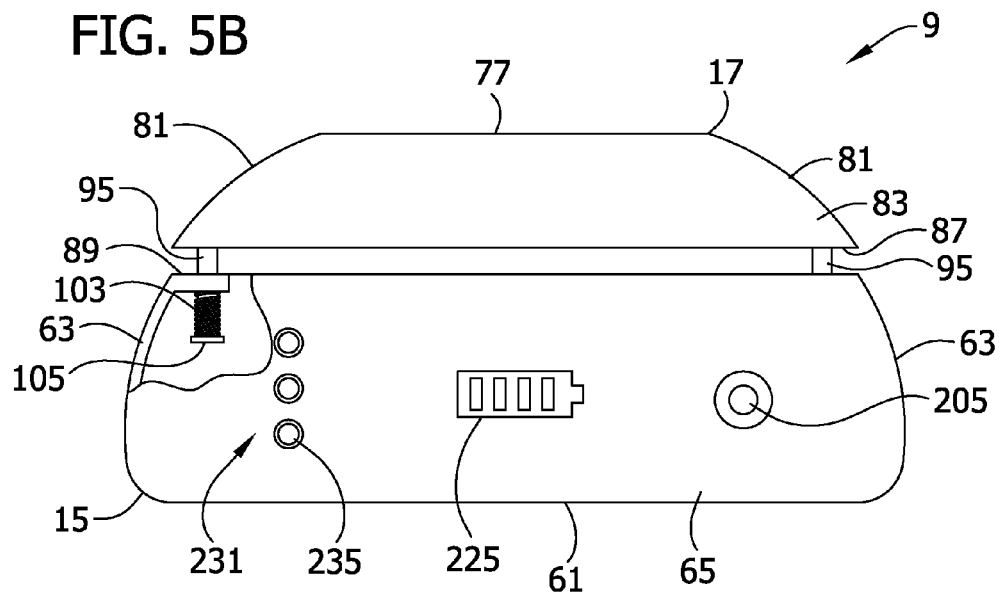
FIG. 5B is a view similar to FIG. 5A but showing the housing in an expanded condition.

Referring to FIGS. 4, 5A and 5B, it will be observed that the base and cover members 15, 17 of the housing 9 are guided between their contracted and expanded positions by a number of pins 95 extending down from the rim 87 of the cover member through guide holes 99 in the rim 89 of the base member. (Alternatively, the guide pins can extend up from the base member 15 through holes in the rim 87 of the cover member 17.) The base and cover members 15, 17 are urged toward their contracted position by springs 103 surrounding the pins 99, each spring reacting at one end against the underside of the rim 89 of the base member 15 and at its other end against a stop 105 on the pin. Other guide and/or spring arrangements can be used. In some embodiments, the springs 103 are eliminated entirely, since the base and cover members 15, 17 of the housing will move back toward their contracted position automatically as the actuator 21 moves back to a position corresponding to the contracted position of the housing.

Referring to FIG. 4, the actuator 21 is shown to be a mechanical actuator contained entirely within the housing 9, i.e., within the space defined by the opposing housing members 15, 17. The actuator 21 of this particular embodiment is a non-pneumatic actuator, i.e., it does not include any components requiring the use of pressurized air or gas for operation. As illustrated in FIG. 4, the actuator 21 includes a pair of cam shafts 115 having cams 121 mounted at one end thereof, a prime mover comprising a reversible electric motor 125 (e.g., a small DC motor) having an output shaft 127, and a gear train, generally designated 131, connecting the output shaft of the motor to the two cam shafts. As shown best in FIGS. 6 and 7, the gear train 131 comprises a pair of cam gears 135 rigidly affixed to respective cams 121, a directional gear 141 in mesh with one of the two cam gears 135, and a pinion gear 145 on the output shaft 127 of the motor 125 in mesh with the directional gear 141 and the other of the two cam gears 135. Two additional cams 121 are mounted on the opposite ends of the cam shafts 115, such that there are a total of four cams located for engaging the cover member 17 of the housing 9 at intervals spaced around the cover member to more evenly distribute the force applied by the actuator 21 over a greater area of the cover member. The number of cams 121 used can vary, four being shown for purposes of illustration only. The gears and cams are preferably (but not necessarily) of a suitable plastic for quiet operation.

The arrangement shown in FIG. 4 is such that rotation of the motor output shaft 127 causes the two cam shafts 115 to rotate in opposite directions. The two cams 121 on each cam shaft 115 are shaped and contoured for contact with the bottom surfaces of the curved side walls 81 of the cover member 17 (or other downwardly facing surfaces of the cover member) such that rotation of the motor output shaft 127 in one direction causes the cams 121 to rotate, e.g., through a partial revolution, to increase the separation between the two housing members 15, 17 against the urging of the springs 103 to expand the overall dimension of the housing 9 from D1 (FIG. 6) to the larger dimension indicated at D2 in FIG. 7. To contract the housing members 15, 17, the motor 125 rotates the output shaft 127 in the reverse (opposite) direction to move the cams 121 back to their initial (FIG. 6) position. This allows the two housing members to move back toward one another to contract the overall dimension of the housing 9 from D2 to D1. The magnitudes of the distances D1 and D2 will vary depending on a variety of factors, such as the size and configuration of the base and cover members 15, 17 of the housing, and the "throw" of the cams 121 as determined by the contour of their cam surfaces and the extent of rotary movement of the cam shafts 115. In general, however, the system should be configured such that the housing members 15, 17 expand a distance sufficient to apply the necessary compression to a limb and contract a distance sufficient to relieve such compression.

It will be understood that the actuator 21 described above is only exemplary and that other actuators can be used for effecting relative movement between the housing members without departing from the scope of this invention. Preferably, the actuator is non-pneumatic so that the compression device is entirely self-contained, i.e., all components for effecting cyclic compression are contained in a single garment which can be applied and removed as a unit from the patient. It is also preferred that the actuator be operable to rapidly expand and contract the housing 9 in an energy efficient manner.

The compression device 1 further comprises a control system, generally designated 201 (see FIGS. 4 and 4A), for controlling the operation of the device, including an on-off switch 205 positioned on the base member 15 of the housing 9 for convenient access and suitable electronics 211 located in the second compartment 71 of the base member 15 for controlling operation of the motor 125. A power source comprising a battery 221 is also located in the second compartment 71 for supplying power to the motor 125 and other electrical components. The battery 221 can be an off-the-shelf item or custom designed, and it can be disposable or rechargeable. A battery charge indicator 225 is provided on the base member 15 of the housing 9 for indicating the remaining charge (useful life) of the battery 221.

Figure 4A:
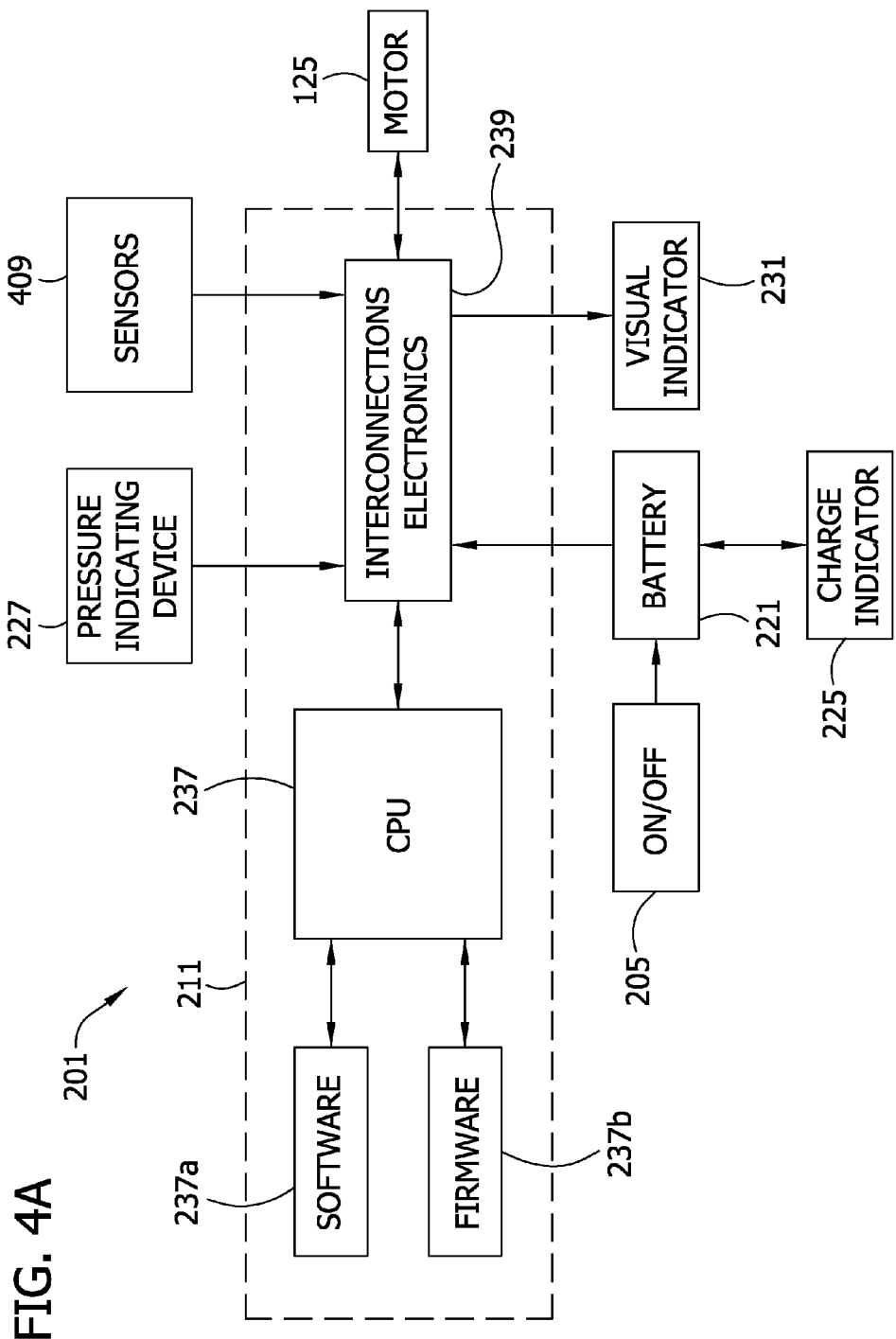
FIG. 4a is an exemplary block diagram of a control system for controlling operation of one or more compression devices of this invention.

FIG. 4A illustrates the control system 201 according to an embodiment of the invention. It will be understood that control system 201 is merely exemplary and that other control circuitry known to those skilled in the art can be used for controlling operation of device 1 generally and effectuating control of motor 125 particularly. The control system 201 desirably includes one or more devices 227 for indicating (either directly or indirectly) the pressure exerted by the compression device 1 on the limb 3 of a patient.

In one embodiment, this indicating device 227 senses a characteristic indicative of the actual pressure applied to the limb. By way of example, the device 227 may comprise a suitable circuit for monitoring the amount of current and/or voltage to the electric motor 125, which amount is proportional to the actual pressure applied to the limb. Alternatively, the pressure-indicating device may comprise one or more pressure sensors for sensing the pressure in one or more chambers in the cushion 49 (if a sealed bladder-like cushion is used), the sensed pressure being proportional to the actual pressure applied to the limb. In still another embodiment, the pressure-indicating device 227 may comprise one or more strain gauges on the band 27, the tension in the band being indicative of the actual pressure on the limb. Other devices for indicating the pressure applied to the limb may be used.

Preferably, the control system 201 also includes a visual indicator 231 for indicating the operational status of the compression device 1. Although various types of visual indicators are contemplated, FIG. 4 illustrates an example comprising an array of tri-color lamps 235 (LED's). The array indicates, among other things, the ON/OFF status of the compression device 1, the status of any ongoing adjustment to a system setting (e.g., a pressure setting), the readiness of the actuator 21 to begin cycling, the status of communication with other compression devices which may be in use (described in more detail later), and an alarm condition. For example, one lamp on (amber) may indicate that the power is on and that one or more setting adjustments are in progress. Two lights on (green) may indicate that the power is on and that all setting adjustments are complete. Three lights on (all green) may indicate that all adjustments are complete and that the compression device is successfully communicating with other compression devices of the system. Three lights on (all red) may indicate an alarm condition. This protocol may vary within the scope of this invention.

Referring again to FIG. 4A, control system 201 further comprises a central processing unit (CPU) 237, such as a microprocessor or the like for executing computer-implemented instructions in the form of software 237a and/or firmware 237b. In one embodiment, the CPU 237 provides control signals to operate the actuator 21 of compression device 1 and to carry out a desired compression treatment regimen (as discussed below). The control signals from CPU 237 may provide distinct compression regimens, depending on the location of compression device 1 on the patient's limb 3 (e.g., attached to the calf at position B or the thigh at position C in FIG. 9). As shown in FIG. 4A, control system 201 communicates with its power source (e.g., battery 221) and visual indicator 231 via interconnection electronics 239. The interconnection electronics 239 send control signals from CPU 237 to the compression device's prime mover (e.g., motor 125) over, for example, electrical or fiber optic lines. In addition, CPU 237 receives information from pressure-indicating devices 227 via interconnection electronics 239 over the same or similar lines. Advantageously, the electronics 211 of control system 201 also communicate with sensing elements 409 (FIG. 11), one or more other compression devices (e.g., modules 321 in FIG. 9), external communications sources (e.g., RF or IR communications), and the like via electronics 239.

Those skilled in the art are familiar with executing software 237a and/or firmware 237b by CPU 237 to perform a number of operations, including but not limited to: controlling the operation of motor 125, including its output shaft 127; communicating with pressure sensing devices 227; controlling charge indicator 225 and/or visual indicator 231; communicating with charge indicator 225; operating actuator 21; and sensing the voltage or current to the motor 125 to indicate a relaxed state of the device 1. As known in the art, a processor such as CPU 237 may further execute computer-implemented instructions in the form of software 237a and/or firmware 237b to control voltage or speed of motor 125 to rotate its output shaft 127 for increasing the throw of the cams 121, thereby increasing D2 to increase the pressure during a compression therapy regimen. Once activated, CPU 237 determines the treatment regimen and begins treating, as described above, by rotating motor 125, which in turns adjusts the throw of the cams 121 for the correct pressure at the device based on its position on the limb (e.g., higher pressure may be desired on the ankle compared to the thigh).

Figure 8:
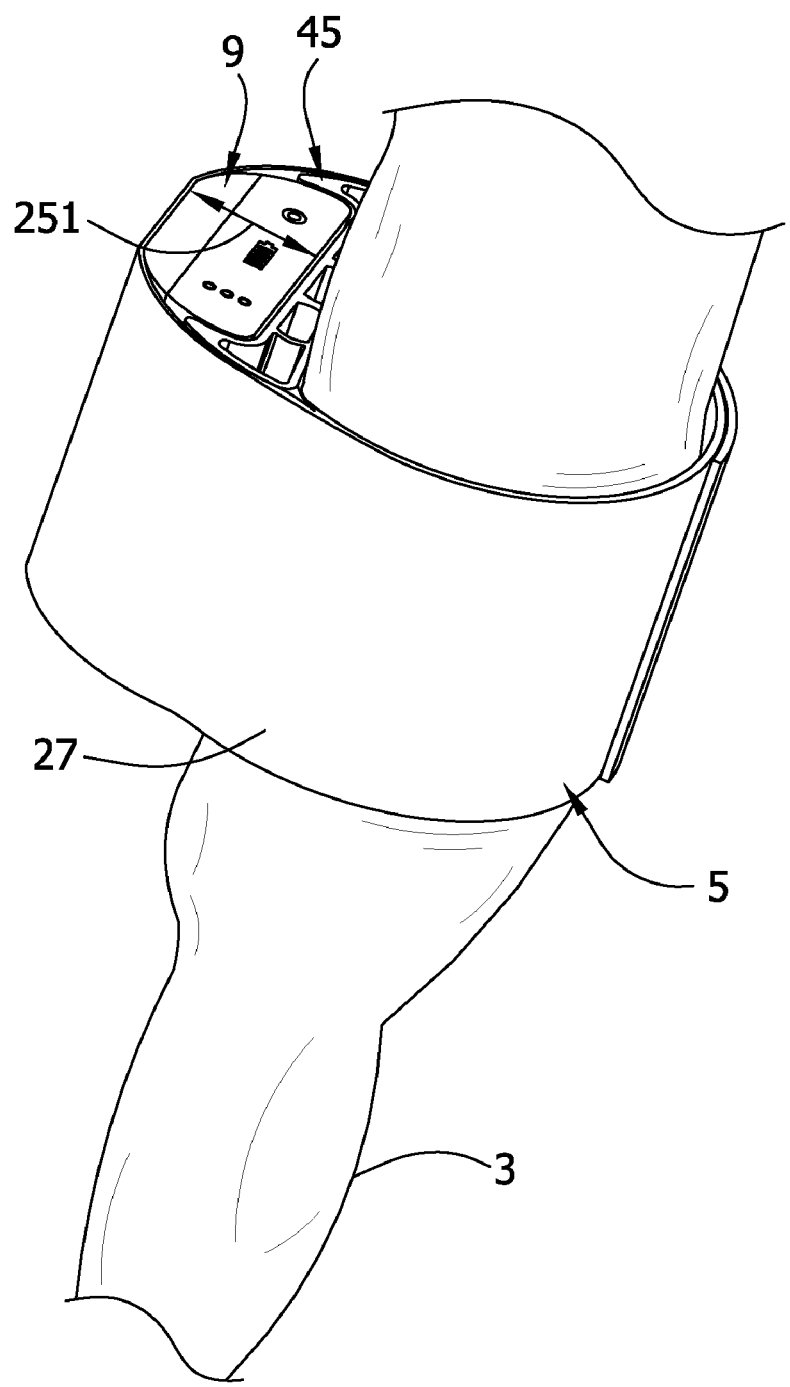
FIG. 8 is a perspective view showing the compression device applied to a limb of a patient.

A typical use of the compression device 1 can be described as follows. Initially, the contracted housing 9 and force-distributing device 45 (if used) are inserted in the pocket 39 of the band 27. The band is then applied to a portion of a limb 3 to be treated, as illustrated for example in FIG. 8. As initially applied, the band 27 should be in a relatively relaxed state or condition applying little if any compressive force to the limb. After all setting adjustments have been made and the compression device is ready for operation, as indicated by the lamp array 235, the control system 201 operates the actuator 21 to expand and contract the housing members 15, 17 through a series of cycles, each cycle comprising a compress stage followed by a relax stage.

During the compress stage, the electric motor 125 is energized to rotate the cam shafts 115 in a first direction, which causes the two housing members 15, 17 to move away from one another, thereby increasing the overall dimension of the housing from D1. As the housing 9 expands, the cover member 17 exerts a force in a direction away from the limb 3 to tension the band 27 and the base member 15 exerts a force in the opposite direction toward the leg. As a result of these forces (indicated at 251 in FIG. 8), the limb is compressed. The force-distributing device 45 functions to distribute the compressive pressure more uniformly across the limb. As the cam shafts 115 continue to rotate, the pressure applied to the limb 3 increases. To prevent over-pressurization, the control system 201 monitors the amount of applied pressure, as indicated for example by the amount of current and/or voltage supplied to the electric motor 125. When a predetermined compressive pressure is reached, the control system de-energizes the motor to stop further rotation of the cam shafts. During this compression stage, the overall dimension of the housing increases from D1 to D2.

After a predetermined compressive pressure is applied to the limb 3 for a duration of time (compress interval), the control system 201 operates the motor 125 to rotate the cam shafts 115 and cams 121 thereon in the opposite direction to contract the housing members 15, 17 and thus reduce the overall housing dimension from D2 back to D1 to relax the pressure on the limb. The relax pressure may range from zero to some pressure greater than zero but less than the compression pressure, as sensed by the current and/or voltage to the motor 125 or by some other suitable means. The relax pressure (if any) is maintained for a period of time (relax interval) sufficient to allow blood to return to the limb. The length of this time period may be fixed (e.g., sixty seconds) or it may vary depending on when a vascular refill condition is detected. In this regard, there is typically some increase in the circumferential size of the limb as blood returns to the compressed portion of the limb. This increase in size can be used to trigger the start of a new cycle. In one embodiment, the pressure sensing device of the control system 201 is used to detect the increase in limb size. For additional details regarding detection of a vascular refill condition, reference may be made to U.S. Pat. No. 6,231,532, assigned to Tyco Healthcare Group LP. This patent is incorporated herein by reference for all purposes not inconsistent with this disclosure.

The cycling continues as described above until the motor is de-energized automatically by the control system 201 or manually by actuating the power switch 205. After use, the housing 9 is removed from the pocket 39 of the band 27 for re-use with a fresh band.

During operation of the device 1, particularly during initial start-up, the compressive pressure applied by the device may need to be adjusted. The control system 201 can make any necessary adjustment by varying the "throw" of the cams 121 until the pressure sensing device of the control system 201 indicates that the desired compressive pressure is being applied. Thus, to increase the pressure, the control system 201 simply operates the motor 125 to rotate its output shaft 127 through a greater number of degrees to increase the throw of the cams 121 and thus increase dimension D2 of the housing 9. To decrease the compressive pressure, the control system 201 operates the motor 125 to rotate its output shaft 127 through a shorter segment of rotation, thereby decreasing the throw of the cams 121 to decrease dimension D2.

Figure 9:
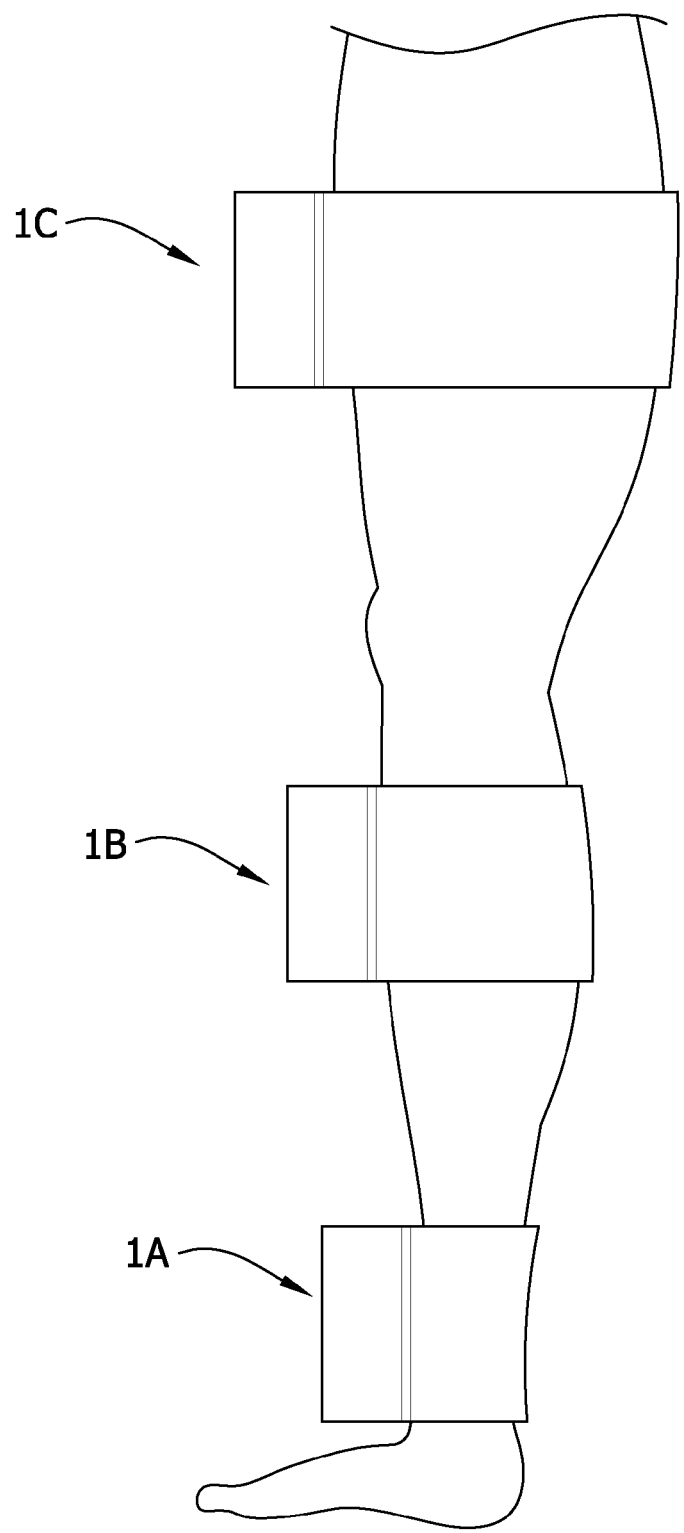
FIG. 9 is a view showing three compression devices of a system of this invention applied to the limb of a patient.

As illustrated in FIG. 9, two or more compression devices (e.g., 1A, 1B and 1C) can be used simultaneously on the limb or limbs of a patient. By way of example, as will be understood by those skilled in this field, a plurality of compression devices 1 can be used on the same limb to cyclically compress different portions of the limb in a sequential manner. Alternatively, the compression devices can be applied to different limbs for compressing the limbs alternately or concurrently or in some other synchronized manner. The compression devices 1A, 1B and 1C may operate completely independent of one another, or they may be under the control of a single integrated control system. If an integrated control system is used, it may be similar to the control system 201 described above for a single compression device but modified to include wireless (e.g., RF) transmitters and receivers and/or other components enabling communication between the multiple compression devices.

In the example of FIG. 9, a first compression device 1A is secured around the ankle for applying a first compressive pressure (e.g., 45 mmHg); a second compression device 1B is secured around the calf for applying a second compressive pressure (e.g., 40 mmHg); and a third compression device 1C is secured around the lower thigh of a patient for applying a third compressive pressure (e.g., 30 mmHg). The devices 1A, 1B, and 1C can be physically interconnected, color-coded, or otherwise identified to indicate where they are to be placed and/or the different compressive pressures they will apply. The integrated control system operates the devices sequentially through a series of cycles, each of which includes a compress stage followed by a relax stage.

During the compress stage of an exemplary cycle, expansion of the ankle compression device 1A is started at time $T_1=0$ seconds, for example, to apply the first compressive pressure; expansion of the calf compression device 1B is started at time $T_2=2.5$ seconds, for example, to apply the second compressive pressure; and expansion of the thigh compression device 1C is started at time $T_3=5.5$ seconds, for example, to apply the third compressive pressure. Each compression device continues to expand until the proper pressure is reached, as sensed by the sensing device incorporated into the control system 201 of the compression device. Further expansion of the compression device is then stopped. There may be some overlap of the times during which the compression devices expand, but in general the compression applied by the devices should occur in a progressive manner to move the blood in the limb in a direction toward the heart.

After the compress stage has ended (e.g., at a cycle time of $T_4=11$ seconds), any further expansion of the compression devices 1A, 1B, 1C is stopped, and the devices are contracted simultaneously to relax or release the pressure on respective portions of the limb. The relax stage preferably continues for an interval of time sufficient to allow blood to return to the limb, as discussed above. A new cycle begins after the relax stage of the previous cycle has ended (e.g., at time $T_5=71$ seconds). The cycles continue to repeat until the compression devices are shut off, which may occur automatically via the control system or by manual operation.

Figure 10:
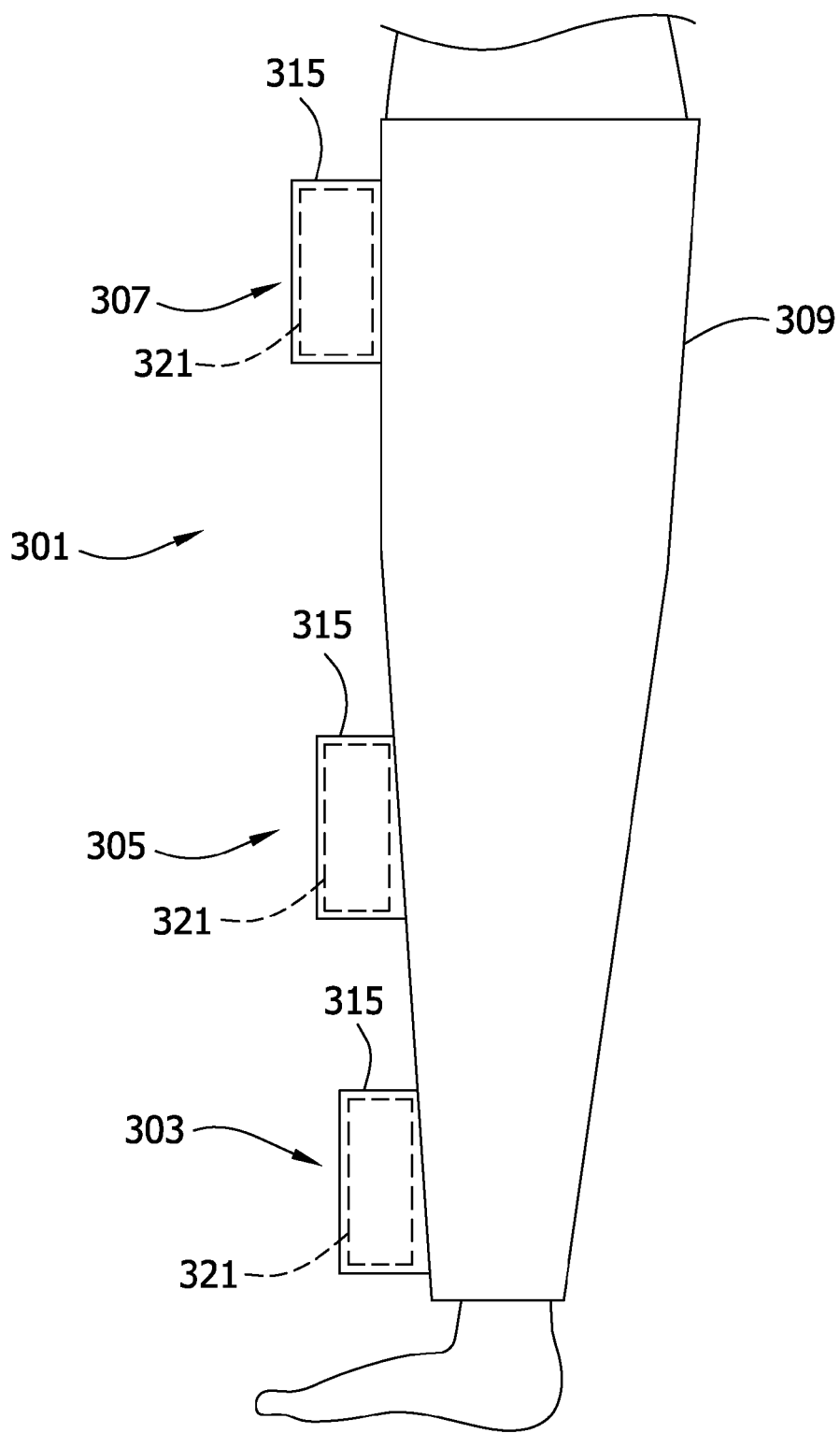
FIG. 10 is a view showing a different embodiment of a compression system comprising an integrated compressive unit and three modules.

FIG. 10 shows another embodiment of a compression system of this invention, generally indicated at 301. The system includes two or more compression devices, three such devices 303, 305, 307 being illustrated. The compression devices are similar to the compression device 1 described above except that the compressive sections are integrated into a single compressive unit 309 sized and shaped for extending generally circumferentially around a limb such as a leg. As used herein, the term "integrated" means any configuration where the compressive sections are physically connected to one another. By way of example, the unit 309 may comprise an elongate panel sized to encircle the limb and to be releasably secured in place by an appropriate number of fasteners along adjacent edges of the panel to form a sleeve around the limb. The compressive unit 309 may have other configurations. Pockets 315 are provided on the unit 309 for removably receiving respective "modules" 321 of the compression devices 303, 305, 307. Each such module 321 includes a housing 9, an actuator 21 and, preferably, a force-distributing device 45, the construction and operation of which are described above. These modules 321 operate to apply compressive pressure to different portions of the limb. The modules 321 may be removably attached or otherwise removably connected to the unit 309 by means other than pockets.

In use, the compressive unit 309 is applied to the limb and the modules 321 are operatively connected to the unit, as by placing the modules in respective pockets of the unit. The modules are then operated to compress respective portions of the limb in a sequential manner, i.e., in a direction toward the heart. This direction is important so as not to cause injury to the patient. After the treatment has ended, the modules 321 are removed from respective compressive sections of the unit 309. The unit 309 is then typically discarded. The modules can be re-used with a different unit 309 holding multiple modules, or with one or more bands each holding only one module. Because the modules 321 can be positioned at different locations with respect to a limb during re-use, it is desirable to have an integrated control system which senses the location of the modules with respect to the limb, and which coordinates the operation of the modules after they have been placed in position so that proper sequential and gradient compression of the limb is achieved. Preferably, the coordination of these modules should not interfere with the operation of other modules applied to a different limb of the same patient or with the operation of other modules on a limb or limbs or a different patient.

Figure 11:
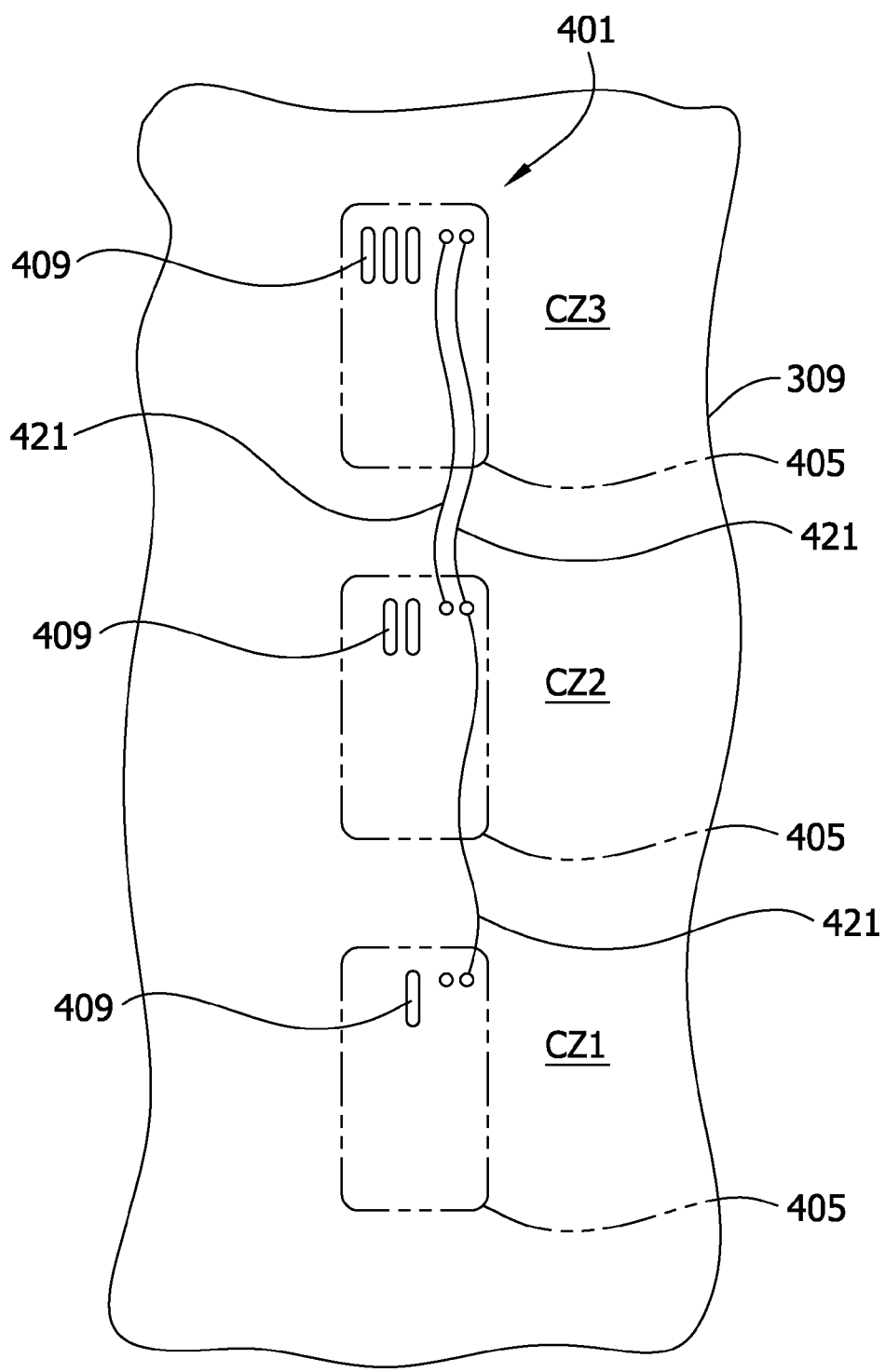
FIG. 11 is a schematic view of an integrated compression unit and elements of an integrated control for controlling the operation of the modules of FIG. 10.

FIG. 11 illustrates an exemplary integrated control system, generally designated 401, for controlling the operation of two or more modules 321 when they are placed on the compressive unit 309. In this embodiment, the compressive unit 309 has three compressive sections or zones CZ1, CZ2 and CZ3 corresponding to different locations on the limb (e.g., ankle, calf and lower thigh), but it will be understood that the number of zones can vary. Each zone comprises a module sensing area 405 at a location where a module 321 is to be placed on the unit 309. This location may correspond to the location of a pocket (e.g., like pocket 39) or other means for operatively and removably connecting the module to the unit 309. The integrated control system 401 comprises location sensing devices on the unit 309 and on the modules 321 (FIG. 10), for sensing the zone (e.g., CZ1, CZ2 or CZ3) in which each module is located when the modules are positioned on the compressive unit 309. In one embodiment, these location sensing devices comprise small sensing elements 409 in the module sensing areas 405 and cooperating sensing elements (not shown) on the modules 321. By way of example, these sensing elements 409 can be magnetic elements secured to the unit 309 for actuating magnet sensing elements on the modules to open or close circuits of the control system 401. Alternatively, the sensing elements 409 can be optical elements on the unit 309 (e.g., areas of different colors or optical patterns) and optical sensing elements on the modules 321 for optically sensing, either reflectively or absorptively, the optical elements on the unit 309. Alternatively, the sensing elements 409 can be electrical contacts on the unit 309 which mate with electrical contacts on the modules 321 when the modules are placed in position on the unit 309. Other sensing elements can be used without departing from the scope of this invention.

The integrated control system 401 also includes means for providing communication between the modules 321. For example, as shown in FIG. 11, electrical or fiber-optic lines 421 may be embedded or otherwise secured to the unit. When positioned on the unit 309, the modules releasably connect with these lines 421 in a suitable manner (e.g., via quick-connect connectors) to provide the communication necessary for providing control information to and from the modules. In FIG. 11, the first (lower) and second (middle) sensing areas 405 are connected by a single pair of communication lines; the second and third (upper) sensing areas 405 are connected by two pairs of communication lines. Other line configurations are possible. Alternatively, communication between the modules may be by wireless RF or IR. Through the use of frequency coded communication transmission, close proximity and/or suitable shielding, the RF or IR communication signal is preferably directed only to the modules 321 on the unit 309 and not to other modules on different limbs or other patients. By means of this communication, the control system 401 is able to coordinate the operation of the modules 321, e.g., the pressure applied by each module to a respective limb portion, the timing of each compression cycle, and the detection, indication and/or correction of various parameters or errors (e.g., pressure, timing).

It will be observed from the foregoing that the integrated control system 401 performs two functions. First, it senses the location of each module 321 with respect to the compression zone in which it is placed. Second, based on this sensed location, the system coordinates the operation of the modules 321 to achieve the desired sequential and gradient compression of the limb.

According to aspects of the invention, the integrated control system 401 cooperates with control system 201, such as shown in FIG. 4A, which may be part of each of the modules 321. In this instance, CPU 237 communicates via interconnection electronics 239 over one or more of the lines 421. The software 239a executed by CPU 237 may be modular such that control system 201 is capable of controlling operation of module 321 in any one of the sensing areas 405. In this embodiment, the CPU 239 is responsive to communications via line 421 and/or sensing elements 409 for identifying the relative position of the associated module 321 and providing control signals as a function of the identified position. Each control system 201 associated with one of the modules 321 operates independently to effectuate a compression regimen in one location on compression unit 309, but its operation is coordinated with that of the control systems 201 associated with other modules 321. As described above, the control signals from each CPU 237 may provide distinct compression regimens, depending on the location of compression device 1 on the patient's limb 3 (e.g., attached to the calf at position B or the thigh at position C in FIG. 9). For example, when control system 201 identifies one or more compression devices 1A, 1B or 1C attached to the patient's limb 3, as in FIG. 9, software 237a causes the control systems 201 to place their associated modules 321 in a standby mode until the user activates one of the modules. Once activated, CPU 237 executes software 237a to determine the treatment regimen for the respective position of the associated module 321 and begins treatment.

In an alternative embodiment, one control system 201 functions as a master controller for controlling operation of all of the modules 321 connected thereto. In another alternative embodiment, the control system 201 associated with one module 321 is responsive to the control system associated with another module 321 as a function of the relative positions of the modules on the patient's limb 3. In yet another alternative embodiment, the integrated control system 401 comprises the control systems 201 associated with the compression devices 1 of modules 321 operating cooperatively.

Figure 12:
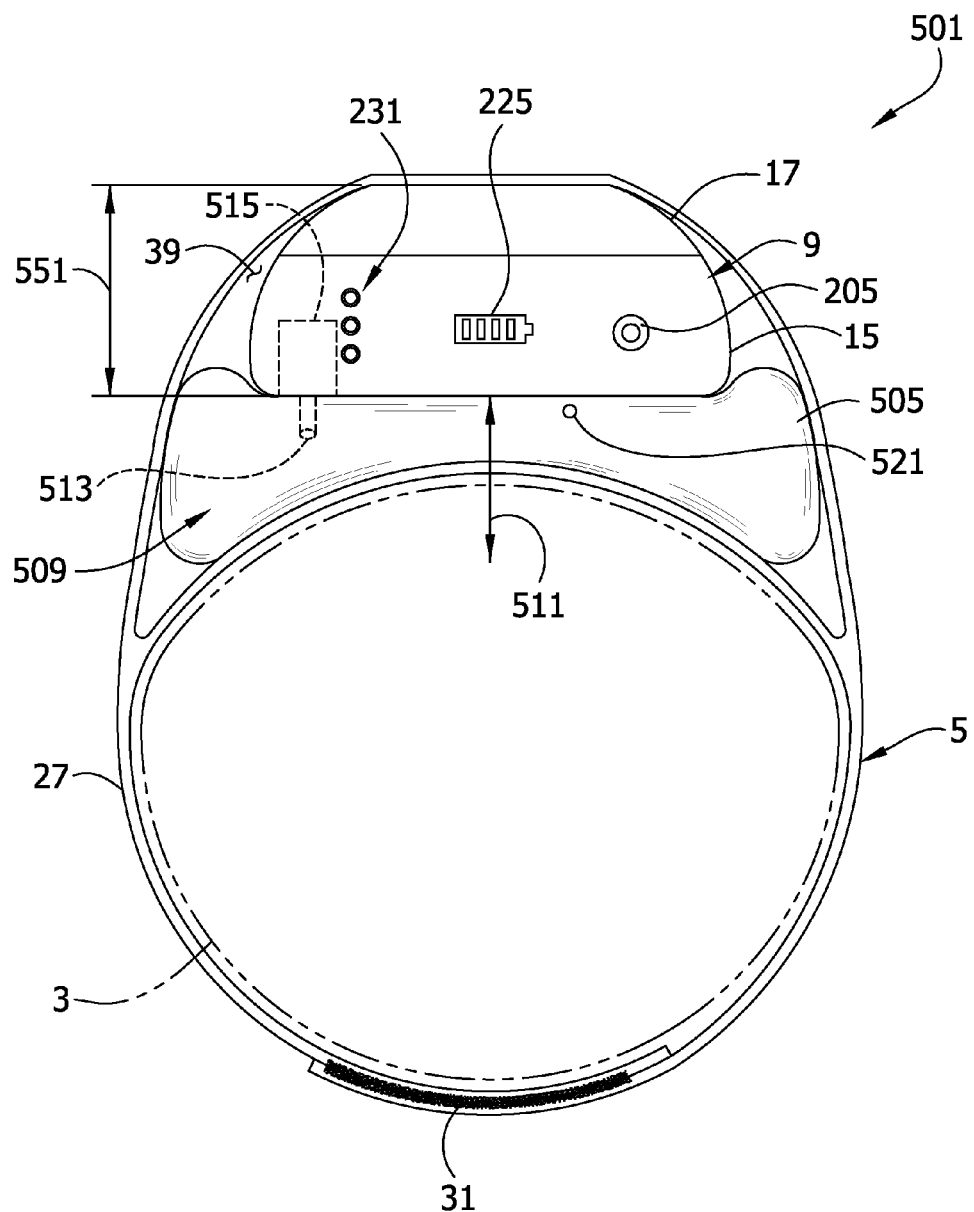
FIG. 12 is an elevational view of a different embodiment of a compression device of this invention, comprising a bladder and a mechanical device for cyclically compressing the limb of a patient (shown in phantom), the mechanical device being shown in a contracted condition.
Figure 12A:
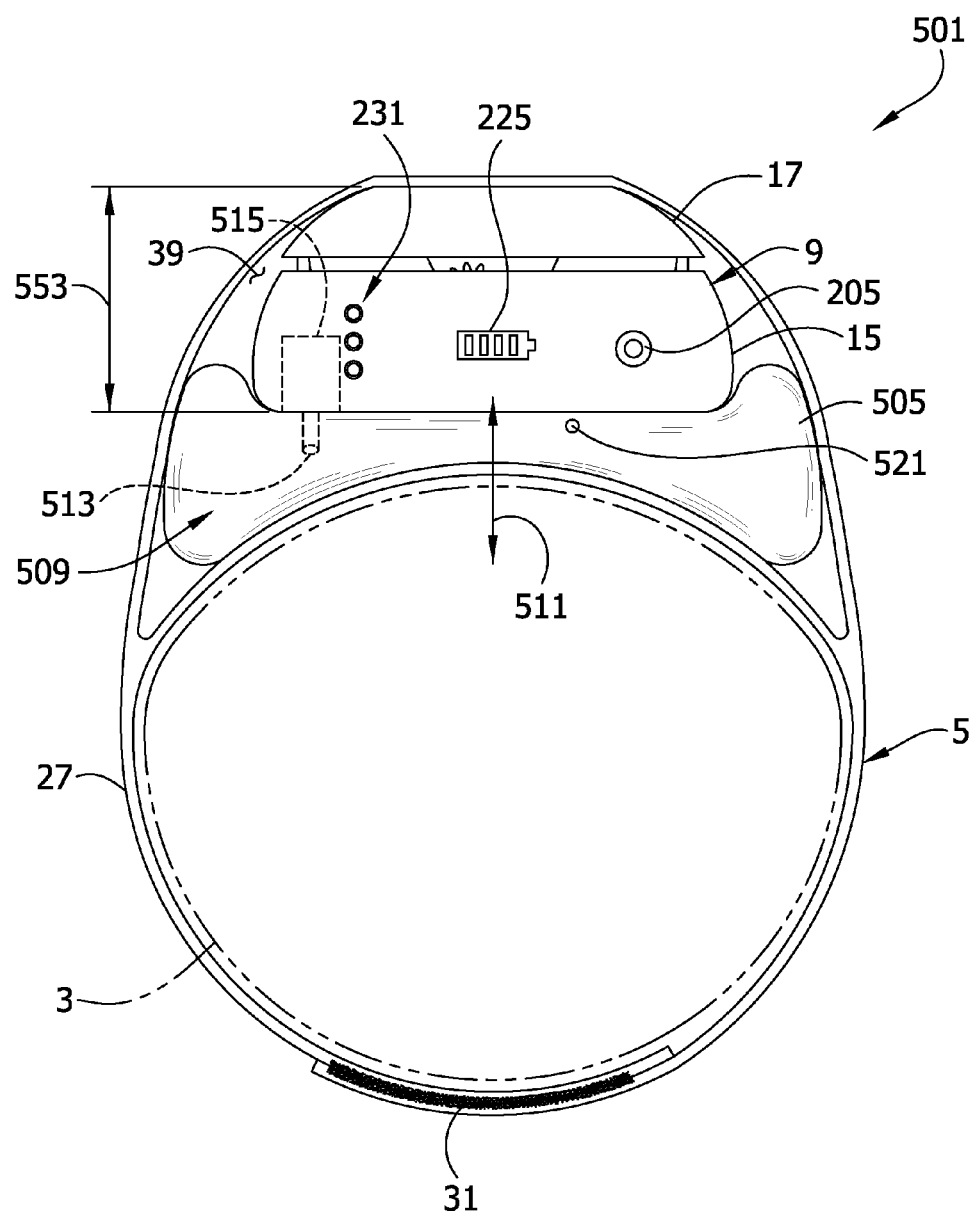
FIG. 12A is a view similar to FIG. 12 showing the mechanical device in an expanded condition.

FIG. 12 illustrates an alternate embodiment of a compression device of this invention, generally designated 501. This device is substantially the same as the compression device 1 of the previous embodiment and corresponding parts are identified by the same reference numbers. In this embodiment, the force-distributing device comprises one or more bladders 505 (only one being shown) filled with air or other suitable gas. The combination of the bladder(s) 505, housing 9 and actuator 21 form a module 509 received (e.g., removably received) in the pocket 39 of the compressive section 5. As described below, the module 509 is adapted for cyclic expansion and contraction in opposite generally radial directions 511 with respect to the limb portion 3 between a contracted condition (FIG. 12) in which the module has a first dimension 551 for relaxing pressure on the limb portion, and an expanded condition (FIG. 12A) in which the module has a second dimension 553 greater than the first dimension for compressing the limb portion.

The bladder 505 provides additional pressure and size adjustment when compressive treatment is provided to the patient. The bladder 505 is a sensing bladder for sensing a characteristic of compression therapy on a patient. The bladder 505 has a sensing device 521 in communication with the contents of the bladder for sensing, for example, the pressure of the contents of the bladder, and for outputting a signal indicative of that characteristic to the control system 201. Placing the sensor in-situ with the bladder medium provides for greater accuracy and control of the compression afforded during treatment. The bladder pressure directly impacts blood flow, in that, a lower pressure distributes less force from the mechanical device to the patient limbs, and likewise a higher pressure distributes a greater amount of the force from the mechanical device to the patient's limb. The ability to adjust the bladder pressure with precision allows the patient to tailor treatment to their comfort level. A patient wearing the device can adjust the nominal pressure, independent of computer instruction operating a therapy regime, as described below in the operation of the device. Other sensing devices for sensing other characteristics of the compression therapy are contemplated. For example, the sensor may be a sensor, in a thin layer composite, between the bladder and the leg for sensing a condition of the patient (e.g., temperature, pulse, blood flow, oxygen level).

The bladder has a pneumatic port 513 and a suitable valve mechanism (not shown) for inflation of the bladder by a pump 515. In FIG. 12, this pump 515 is integral with the compression device 501 and is mounted inside or adjacent the base member 15 of the housing 9 for communication with the port 513. Preferably, the pump 515 is a small pneumatic pump, such as a miniature battery-operated air compressor, which consumes a relatively small amount of power. The power is provided by the battery 221 or a separate power source in the housing 9. Alternatively, the pump used to inflate the bladder can be non-integral with the compression device 501. By way of example, the pump can be a hand pump manually operated by the patient or caregiver. A suitable transducer 521 (e.g., pressure sensor) is provided for sensing pressure of the air (or other gas) in the bladder 505. The bladder 505 can be sized to minimize the distance (e.g., D2 minus D1 in FIGS. 6 and 7) by which the housing parts 15, 17 must expand and contract to effect the necessary cyclic compression. As a result, the size of various components of the actuator 21 (e.g., motor 125, cams 121, gears 135, 141, 145) can be decreased to reduce cost.

In use, one or more of the compression devices 501 are applied to the limb 3 to be treated, as described in the previous embodiments. A nominal pressure is maintained in the bladder(s) 505 to provide for therapy adjustment, to provide a static baseline pressure, and to distribute the compressive forces applied by the compression device 501 evenly about the surface of the leg or limb of a patient. The transducer 521 provides feedback to the controller (e.g., CPU 237 in FIG. 4a) for application of proper therapy to the limb. The pressure in the bladder(s) 505 is maintained by the pump 515. If desired, a pressure relief valve or passively activated check valve (not shown) can be installed to maintain the pressure in the bladder(s) 505 at a pressure no greater than a predetermined pressure.

In operation, the compression device 501 cyclically compresses both the limb and the bladder(s) 505. This action is monitored by the transducer 521 which provides feedback to the controller to monitor and adjust the tension in band 27. Preferably, the aforementioned small nominal pressure is maintained in the bladder 505 during the relax stage of each compression cycle. This pressure is much less than in prior art systems, such as found in U.S. Pat. No. 4,253,449 (Arians et al.) owned by Tyco Healthcare Group LP.

Just before the compress stage of each cycle begins, the pneumatic port 513 of the bladder 505 is closed by a suitable valve mechanism (not shown) or other means to capture the small nominal pressure in the bladder. As the base and cover members 15, 17 of the housing 9 expand, the tension in the band 27 and the pressure in the bladder 505 increase proportionally. The pressure transducer 521 monitors this change in pressure and the peak pressure value is fed into a feedback algorithm executed in one of the software and/or firmware modules 237a, 237b of FIG. 4a. The algorithm functions to compare the peak pressure value to a predetermined (selected) peak value or set point corresponding to the desired maximum pressure to be applied to the limb during the compress stage of each cycle. If the sensed peak pressure is higher than the predetermined set point, then the nominal pressure in the bladder 505 is adjusted downward by venting an appropriate amount of air (or other gas) from the bladder. Conversely, if the sensed peak pressure is lower than the predetermined set point, then the nominal pressure in the bladder 505 is adjusted upward by delivering additional air (or other gas) to the bladder(s). This adjustment process continues for subsequent cycles until the sensed peak pressure value substantially matches the predetermined maximum pressure set point.

In the case of an edematous patient, the level of swelling in a limb or limbs can change over time. An advantage of this compression device 501 is that the pressure in the bladder(s) 505, as sensed by the pressure transducer 521, can be adjusted to reduce or increase the volume contained within the compressive band 27 in a manner which is inversely proportional to the amount of edema change. For example, if the compression device 501 is set to apply a predetermined compressive pressure of 45 mmHg during the compress interval, but the pressure transducer 521 senses a bladder pressure of 50 mmHg due to increased edema, the control system 201 will automatically reduce the pressure in the bladder(s) 505 to compensate for the increased swelling. As a result, blood flow to the swollen limb is not unduly restricted.

The compression device 501 using one or more bladders 505 is also capable of measuring vascular refill time (VRT). VRT measurement is an air plethysmographic technique that determines when the veins of a limb have substantially completely refilled with blood after the compression stage of a compression cycle. See, for example, the VRT measurement described in U.S. Pat. No. 6,231,532 to Watson et al., the entire content of which is incorporated by reference herein. This VRT technique is used to minimize the amount of time that blood remains stagnant in the veins.

In general, a VRT measurement is made during the relax stage of the compression cycle in which the compressive device 501 first reaches its compressive pressure set point. Thereafter, measurements are taken at selected intervals (e.g., every 30 minutes). The measurement process it initiated at $T=T_{start}$ when the sensed pressure in the bladder decreases to a predetermined level (e.g., 5-7 mmHg), indicating the end of the compress stage and the start of the relax stage of the cycle. As blood returns to the limb 3, the limb expands and causes the pressure in the bladder(s) 505 to increase. This pressure increase is sensed over time by the transducer 521. In one example, the bladder pressure is sampled at one-second intervals and the pressure is monitored by using a moving or "rolling" 10-second window of time in which the oldest sample value is dropped from the window and a new sample value is added every second. When the difference between the first and last sample values in the window decreases to a predetermined value (e.g., about 0.3 mmHg), indicating that the refill curve has reached its plateau and that refill is substantially complete, the measurement process is terminated at $T=T_{end}$. The vascular refill time is then determined ($T_{end}$ minus $T_{start}$) and, if necessary, an appropriate adjustment to the relax interval of the compression cycle is then made.

For example, in one embodiment the "default" relax interval is 60 seconds. If the measured VRT is greater than 60 seconds, then the relax interval remains at 60 seconds. If the measured VRT is between 20 and 60 seconds, the relax interval is re-set to the measured VRT. If the measured VRT is less than 20 seconds, then the relax interval is re-set to a minimum time of 20 seconds, for example. The minimum relax interval (e.g., 20 seconds) should be sufficient to insure that the limb has substantially refilled with blood before initiation of the compress stage of the next cycle. The minimum relax interval may also be established by adding a predetermined safety factor (e.g., 5 seconds) to the measured VRT.

Under certain circumstances, the VRT measurement may be disregarded. For example, such circumstances might include a situation where the standard deviation of the pressure values in the sample window exceed a predetermined maximum standard deviation, indicating that the VRT measurement is erroneous; or a situation where the sensed pressure in the bladder(s) 505 falls below a predetermined minimum value (e.g., 2 mmHg) during the measurement process, indicating a possible leak in the system; or a situation where the sensed pressure in the bladder(s) 505 exceeds a predetermined value (e.g., 20 mmHg) during the measurement process. In such situations the VRT measurement is disregarded, and the relax interval of the prior cycle continues to be used.

As explained in regard to the first embodiment, more than one compression device 501 can be used to sequentially compress different portions of the same limb (e.g., one leg) or different limbs (e.g., two legs). If more than one device 501 is used, the VRT is determined separately for each limb portion being compressed. Preferably, the longest of the measured vascular refill times is then used as the new relax interval for all of the compression devices. The VRT measurements for the compression devices are made (i.e., started and stopped) independent of one another. Preferably, however, any adjustment to the relax interval of the compression devices is not made until after the VRT measurements have been completed for all devices.

As an enhanced safety feature, the control system 201 of the compression system 501 may provide an audible and/or visual error alarm for one or more of the following error conditions: high pressure error, including a sensed pressure greater than a set maximum pressure; low pressure error, including a sensed pressure less than a set minimum pressure (e.g., also detecting the absence of bands or sleeves); system pressure error, including a pressure sensed during a compress stage and/or relax stage of a compression cycle outside of desired parameters; valve error; software error; pump error; vent and deflation error; battery error; and temperature error, including temperatures detected outside of specified environmental conditions. (The compression device 501 can be modified to include one or more temperature sensors to provide the latter feature.) An alarm system of the type described advantageously enhances the safety of the patient during vascular therapy. In the event of an alarm condition, it is contemplated that the visual indicator 231 or other means may flash error signals, sound a continuous alarm, or otherwise indicate an alarm situation. Further, the control system 201 may be responsive to an alarm condition to deflate the bladder(s) 505 and cease further operation of the compression device 501.

Figure 13:
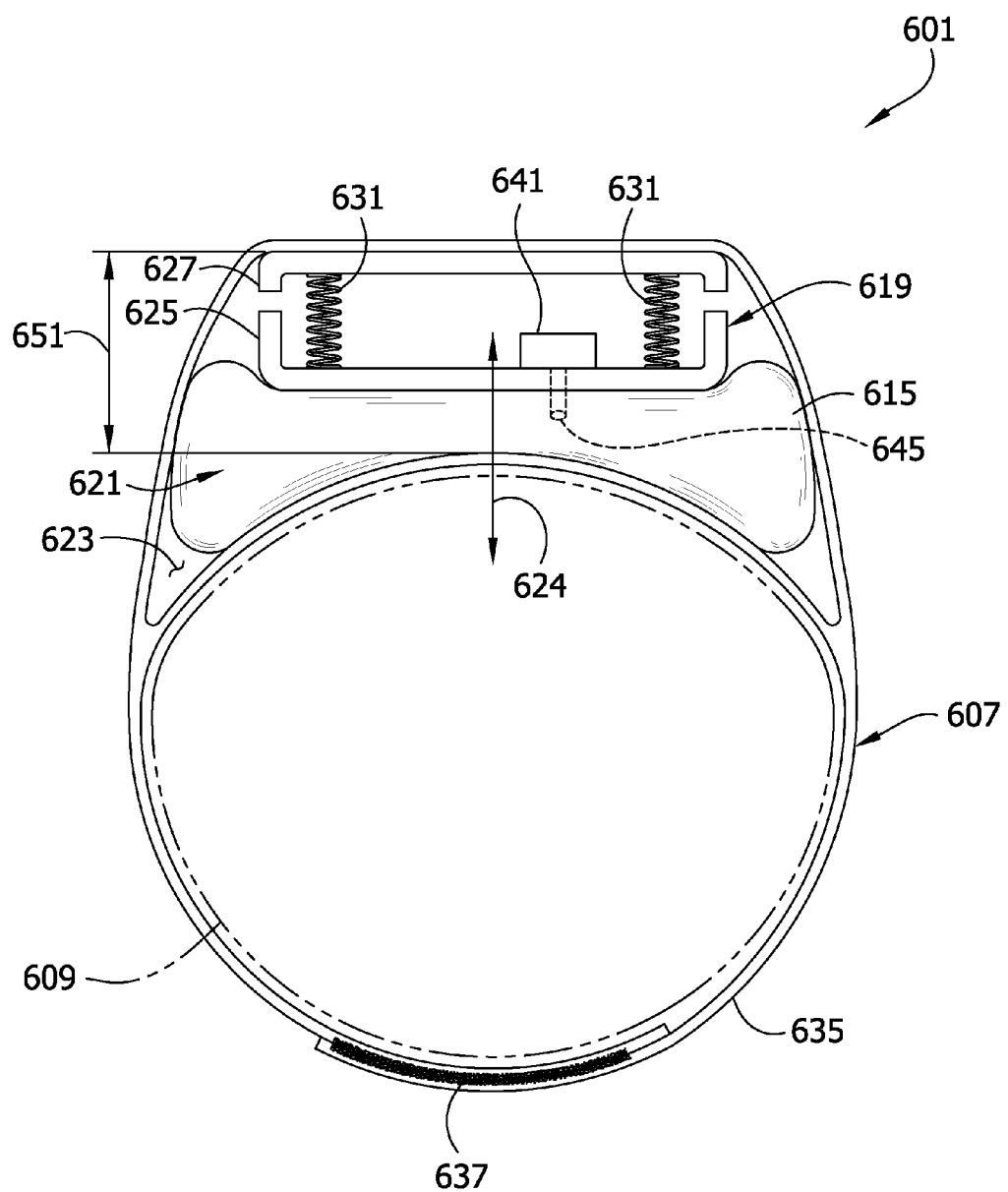
FIG. 13 is an elevational view of another embodiment of a compression device of this invention, comprising a bladder and a different mechanical device for cyclically compressing the limb of a patient (shown in phantom), the bladder being shown in a contracted condition.
Figure 13A:
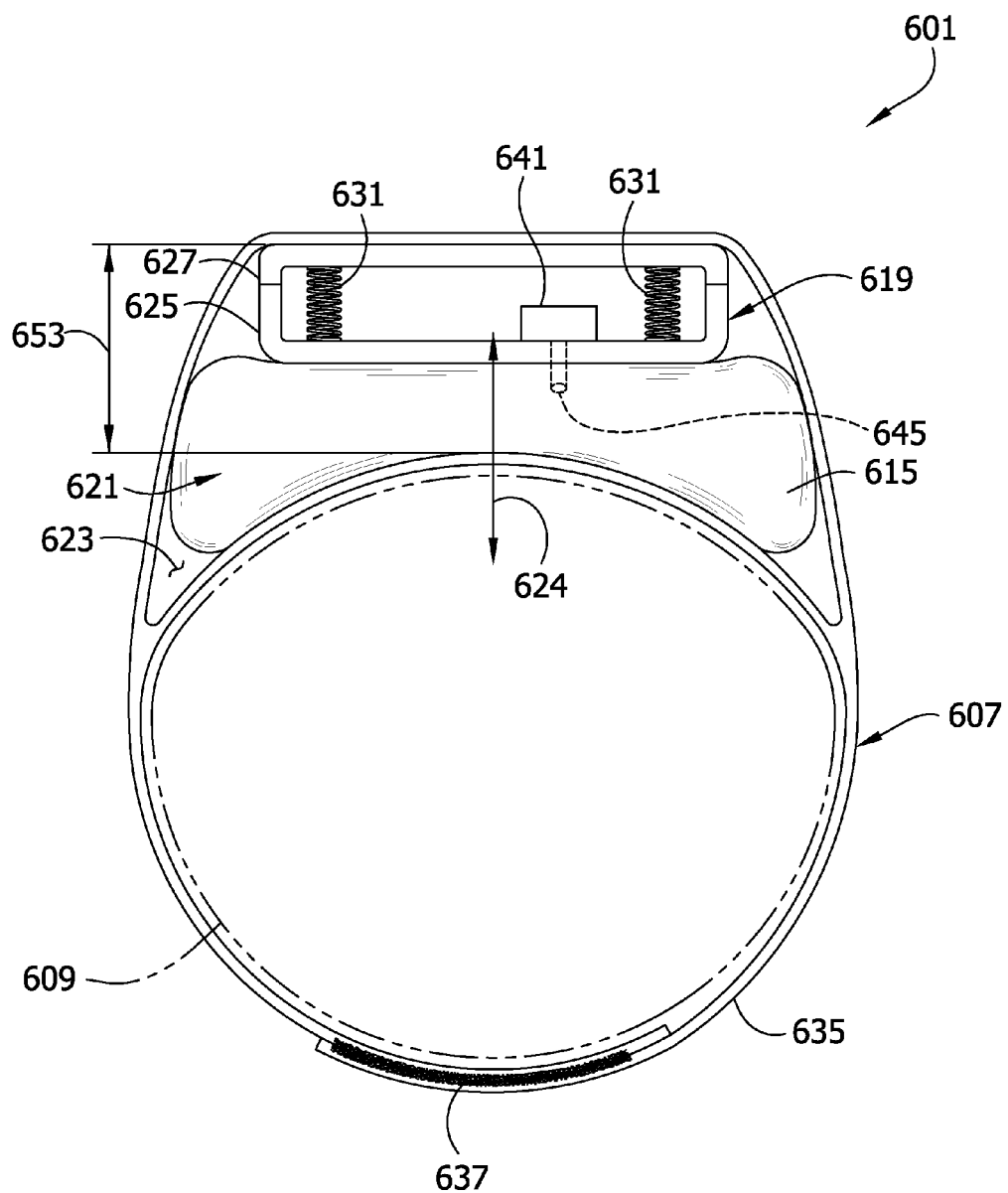
FIG. 13A is a view similar to FIG. 13 showing the bladder in an expanded condition.

FIG. 13 illustrates a third embodiment of a compression device of this invention, generally designated 601. This embodiment is similar to the previous embodiment 501 in that it comprises a compressive section 607 adapted to extend around a portion 609 of a limb, at least one pneumatic bladder 615, and a non-pneumatic mechanical device, generally designated 619. The bladder(s) 615 and mechanical device 619 combine to form a module 621 which is received (e.g., removably received) in a pocket 623 on the compressive section 607. The module 621 may be operatively connected to the compressive section 607 in other ways. As described below, the module 621 is adapted for cyclic expansion and contraction in opposite generally radial directions 624 with respect to the limb portion 609 between a contracted condition (FIG. 13) in which the module has a first dimension 651 for relaxing pressure on the limb portion, and an expanded condition (FIG. 13A) in which the module has a second dimension 653 greater than the first dimension 651 for compressing the limb portion.

In one embodiment, the compressive section 607 comprises a band member 635 having opposite ends which are releasably connected by a suitable fastening device 637 (e.g., similar to 31 in the first embodiment) to form an annular band around the limb. The compressive section 607 may have other configurations.

The mechanical device 619 is non-pneumatic in the sense that it does not include pneumatic components requiring or involving the use of pressurized air or other gas. In the embodiment of FIG. 13, the device 619 includes an inner platen 625 seated on the bladder 615, an opposing outer platen 627, and one or more springs 631 between the platens urging the platens away from one another. The springs 631 of the mechanical device 619 generate a force tending to move the outer platen 627 in a direction away from the limb to expand the module 621 and thereby tension (tighten) the band member 635 around the limb. In this embodiment, the limb is cyclically compressed by varying the pressure in the bladder(s) 615 to expand and contract the bladder. The pressure may be varied by cycling the operation of a small pneumatic pump 641, such as a miniature battery-operated compressor mounted on or adjacent the inner platen 625. The pump 641 communicates with a pneumatic port 645 on the bladder(s). A pressure sensor (not shown) monitors the pressure in the bladder(s) 615. A pressure relief valve or passively activated check valve (not shown) can be installed to maintain the pressure in the bladder(s) 615 at a pressure no greater than a predetermined pressure.

In operation, the pump 641 inflates the bladder(s) 615 which causes the module 621 to expand to compress the limb portion 609 to a predetermined pressure during a compress stage of the compression cycle. The pump 641 deflates the bladder(s) 615 to a predetermined pressure after an appropriate compress interval has ended. This causes the module 621 to contract for relieving the pressure on the limb during the relax stage of the compression cycle. As indicated at 624 in FIG. 13, the module 621 expands and contracts in opposing generally radial (not circumferential) directions relative to the limb portion 609.

Figure 14:
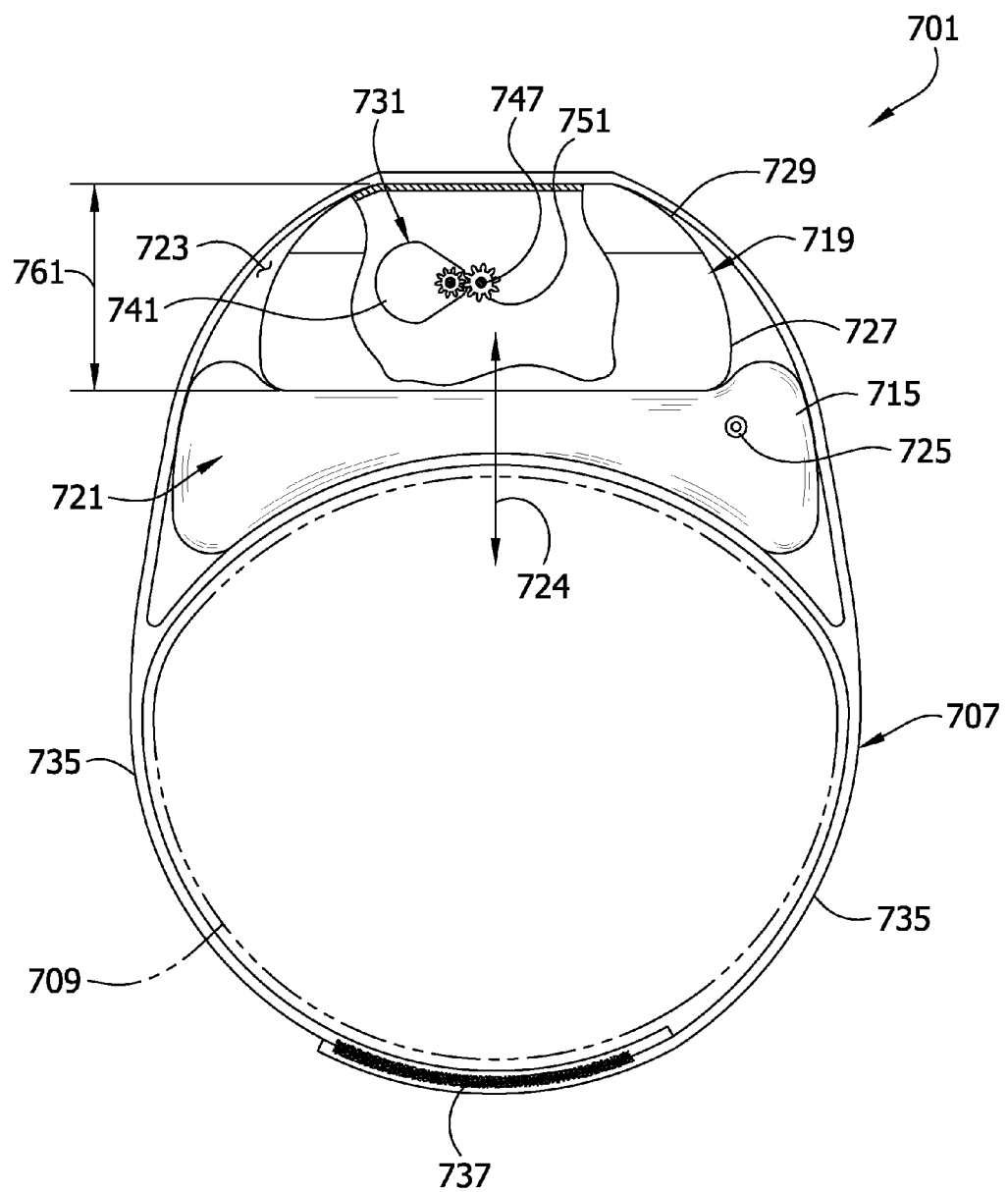
FIG. 14 is an elevational view of still another embodiment of a compression device of this invention, comprising a bladder and a different mechanical device for cyclically compressing the limb of a patient (shown in phantom), the mechanical device being shown in a contracted condition.
Figure 14A:
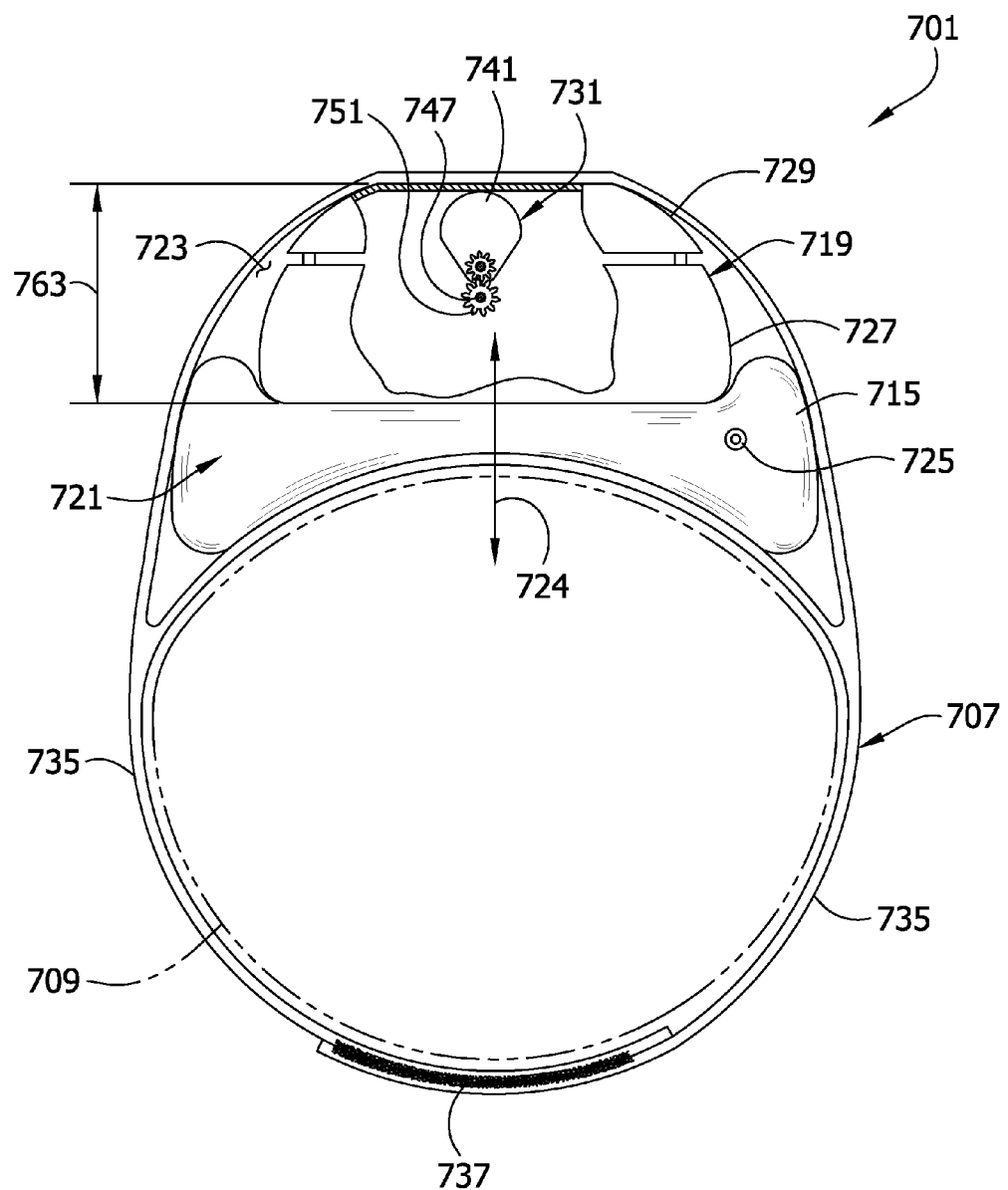
FIG. 14A is a view similar to FIG. 14 showing the mechanical device in an expanded condition.

FIG. 14 illustrates a fourth embodiment of a compression device of this invention, generally designated 701. This embodiment is similar to the compression device 501 previously described in that it comprises a compressive section 707 adapted to extend around a portion 709 of a limb, at least one pneumatic bladder 715, and a non-pneumatic mechanical device, generally designated 719. The bladder(s) 715 and mechanical device 719 combine to form a module 721 which is received (e.g., removably received) in a pocket 723 on the compressive section 707. The module 721 may be operatively connected to the compressive section 707 in other ways. As described below, the module 721 is adapted for cyclic expansion and contraction in opposite generally radial directions 724 with respect to the limb portion 709 between a contracted condition in which the module has a first dimension 761 for relaxing pressure on the limb portion, and an expanded condition (FIG. 14A) in which the module has a second dimension 763 greater than the first dimension for compressing the limb portion.

In one embodiment, the compressive section 707 comprises a band member 735 having opposite ends which are releasably connected by a suitable fastening device 737 (e.g., similar to 31 in the first embodiment) to form an annular band around the limb. The compressive section 707 may have other configurations.

The bladder(s) 715 is positioned between the limb portion 709 and the mechanical device 719. The bladder(s) has a pneumatic port 725 for inflation and deflation of the bladder, as by a hand pump manually operated by the patient or caregiver.

The mechanical device 719 is non-pneumatic in the sense that it does not include pneumatic components requiring or involving the use of pressurized air or other gas. In the embodiment of FIG. 14, the device 719 includes a housing comprising a base housing member 727 seated on the bladder 715, an opposing cover housing member 729, and an actuator 731 inside the housing for moving the housing members toward and away from one another, as described in regard to compression device 501. In the illustrated embodiment, the actuator 731 comprises one or more cams 741 movable between a first position (shown in solid lines in FIG. 14) in which the housing members 727, 729 are relatively closely spaced in a contracted position or condition, and a second position (shown in phantom lines in FIG. 14) in which the members 727, 729 are spaced farther apart in an expanded position or condition. The cam 741 is rotated between its first and second positions by a prime mover (e.g., a small DC motor, not shown) having an output 747 which is connected to the cam 741 by a gear train 751 or other suitable means. The cam(s) 741, prime mover and gear train 751 are located inside the base housing member 727, similar to the compression devices 1, 501 described above. The "throw" of the cam(s) 741 may be adjustable, as described previously. Alternatively, it may be non-adjustable to reduce cost. A pressure sensor (not shown) monitors the pressure in the bladder(s) 715. Alternatively, to reduce cost, a pressure relief valve or passively activated check valve (not shown) can be installed to maintain the pressure in the bladder(s) 715 at a pressure no greater than a predetermined pressure.

To operate the compression device 701, the bladder(s) 715 is inflated to a suitable pressure using the pneumatic port 725. The actuator 731 is then energized to move the base and cover members 727, 729 toward and away from one another to expand and contract the module 721 to conduct successive compression cycles on the limb portion 709. As indicated at 724 in FIG. 14, the module 721 expands and contracts in opposite generally radial (not circumferential) directions relative to the limb portion 709. During this operation, the pressure in the bladder(s) 715 can be adjusted, if necessary.

In at least some of the bladder embodiments described above, the cost of the compression device can be reduced to a point where the entire device can be discarded after a single use. A disposable device has several benefits. First, it is more hygienic for the patient population. Further, the cost of reprocessing the device or components of the device is eliminated. Also, due to the reduced size and weight of the various components, the device is more portable. The bladder embodiments described above are, for the most part, "self-contained", meaning that all components of the compression apparatus and the control are located on the garment worn by the patient.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A compression device for cyclically compressing the limb of a patient to improve blood flow in the limb, the compression device comprising:

a compressive section sized and shaped for extending generally circumferentially around a portion of the limb for applying compressive circumferential pressure to the limb portion;

a housing operatively connected to the compressive section, said housing including first and second rigid housing members combining to define an interior housing space, said first and second rigid housing members being movable relative to each other between a contracted position in which the housing has a first dimension for relaxing said circumferential pressure on said limb portion, and an expanded position in which the housing has a second dimension greater than said first dimension for compressing the limb portion circumferentially of the limb portion; and a non-pneumatic mechanical actuator comprising an electric motor in said interior housing space for cyclically moving the first and second housing members from said contracted position to said expanded position.

2. A compression device as set forth in claim 1 wherein the compressive section is operatively connected to the second housing member for movement therewith relative to the first housing member.

3. A compression device as set forth in claim 2 wherein the housing is adapted to be mounted on the limb between the compressive section and the limb portion.

4. A compression device as set forth in claim 1 wherein the device is configured for venous refill detection.

5. A compression device as set forth in claim 1 further comprising a force-distributing device adapted to be mounted on the limb between said housing and said limb portion.

6. A compression device as set forth in claim 5 wherein said force-distributing device comprises a cushion.

7. A compression device as set forth in claim 1 further comprising one or more springs for urging the housing members toward said contracted position.

8. A compression device as set forth in claim 1 wherein the actuator comprises a cam movable by said electric motor for effecting relative movement between the first and second housing members.

9. A compression device as set forth in claim 8 wherein said electric motor is a reversible electric motor.

10. A compression device as set forth in claim 8 wherein said cam is rotatable by said electric motor to contact an interior surface of one of said housing members to effect relative movement between said housing members.

11. A compression device as set forth in claim 10 further comprising a gear train connecting an output of said electric motor to said cam for rotating the cam.

12. A compression device as set forth in claim 1 further comprising a control system for controlling the operation of said compression device, said control system comprising a device for indicating the amount of compressive pressure applied to the limb portion.

13. A compression device as set forth in claim 12 wherein the pressure-indicating device senses the electrical current or voltage to the motor for providing a control signal to change the amount of pressure applied to the limb.

14. A compression device as set forth in claim 12 wherein said control system is responsive to the applied compressive pressure reaching a predetermined pressure to cause said actuator to cease further expansion of the first and second housing members.

15. A compression device as set forth in claim 1 wherein said first and second housing members have a telescoping fit as they move between said contracted and expanded positions.

16. A compression device as set forth in claim 1 wherein said actuator comprises a first pair of cams mounted on a first cam shaft rotatable by said electric motor to contact an interior surface of one of said housing members to effect relative movement between said housing members.

17. A compression device as set forth in claim 16 further comprising a gear train connecting an output of said electric motor to said first cam shaft for rotating the cam shaft and said first pair of cams.

18. A compression device as set forth in claim 16 wherein said actuator further comprises a second pair of cams mounted on a second cam shaft rotatable by said electric motor to contact an interior surface of one of said housing members to effect relative movement between said housing members.

19. A compression device as set forth in claim 18 further comprising a gear train connecting an output of said electric motor to said first and second cam shafts for rotating the cam shafts and said first and second pairs of cams.

20. A compression device as set forth in claim 1 wherein said interior housing space expands and contracts as said first and second rigid housing members move between said expanded and contracted positions.

21. A compression device as set forth in claim 20 wherein said first and second housing parts are movable in generally radial directions with respect to said limb portion.

22. A compression device as set forth in claim 1 wherein said compressive section comprises an annular band having an annular exterior layer defining an interior space and an interior layer dividing the interior space into a first area for receiving said limb portion and a second area forming a pocket for receiving said housing therein, and a fastening device for securing the annular band around said limb portion in a position in which expansion and contraction of the housing members compresses said limb portion around the entire circumference of the limb portion.

23. A compression device as set forth in claim 22 wherein said housing is removable from the pocket for re-use with a different annular band.

24. A compression device as set forth in claim 23 further comprising a force-distributing device in said pocket.

25. A compression device for cyclically compressing the limb of a patient to improve blood flow in the limb, the compression device comprising:
   a compressive section comprising a generally annular band sized and shaped for extending generally circumferentially around a portion of the limb for applying compressive pressure to the limb portion;
   a housing operatively connected to the compressive section, said housing including first and second housing members combining to define an interior housing space, said first and second housing members being movable relative to each other between a contracted position in which the housing has a first dimension for relaxing pressure on said limb portion, and an expanded position in which the housing has a second dimension greater than said first dimension for compressing the limb portion; and
   a non-pneumatic mechanical actuator comprising an electric motor in said interior housing space for cyclically moving the first and second housing members from said contracted position to said expanded position, and
   a pocket on an interior surface of the band for removably receiving said housing therein.

26. A compression system for cyclically compressing the limb or limbs of a patient to improve blood flow in each of said limbs, the compression system comprising:
   at least two compressive devices for cyclically compressing portions of said limb or limbs, each compressive device comprising:
   a compressive section sized and shaped for extending generally circumferentially around a respective limb portion for applying circumferential pressure to the limb portion,
   a housing operatively connected to the compressive section, said housing including a first rigid housing member and a second rigid housing member combining to enclose an interior housing space, said first and second rigid housing members being movable relative to each other between a contracted position in which the housing has a first dimension for relaxing said circumferential pressure on said limb portion, and an expanded position in which the housing has a second dimension greater than said first dimension for compressing the limb portion circumferentially of the limb portion, and a non-pneumatic actuator comprising an electric motor housed in said interior housing space for cyclically moving the first and second housing members from said contracted position to said expanded position.

27. A compression system as set forth in claim 26 wherein the compressive section of each compression device is operatively connected to the second housing member for movement therewith relative to the first housing member.

28. A compression system as set forth in claim 27 wherein the housing is adapted to be mounted on the respective limb between the compressive section and the respective limb portion.

29. A compression device as set forth in claim 26 further comprising one or more springs for urging the housing members toward said contracted position.

30. A compression system as set forth in claim 26 wherein the actuator comprises a cam movable by said electric motor for effecting relative movement between said first and second housing members.

31. A compression system as set forth in claim 26 further comprising a pocket on said compressive section of each compression device for removably receiving a respective housing.

32. A compression system as set forth in claim 26 wherein said compressive sections of said at least two compression devices are integrated to form a single compressive unit having different compression zones corresponding to different portions of a limb.

33. A compression system as set forth in claim 32 wherein the housing and actuator of each compression device combine to form a module for placement in a respective zone of said compressive unit, and further comprising cooperating sensing devices in said zones and on the modules for sensing the zone in which each module is located when the modules are positioned on the compressive unit.

34. A compression system as set forth in claim 33 further comprising means enabling the modules to communicate with one another.

35. A compression system as set forth in claim 34 further comprising a plurality of control systems each associated with one of the compressive devices, said control systems communicating with each other via said enabling means for determining the zone in which each module is located when the modules are positioned on the compressive unit and for controlling the associated compressive device as a function of the determined zone.

36. A compression system as set forth in claim 26 further comprising an integrated control system for controlling the operation of said at least two compressive devices.

37. A method of using a compression device to cyclically compress the limb of a patient to improve blood flow in the limb, said compression device comprising a compressive section sized and shaped for extending generally circumferentially around a portion of the limb for applying compressive circumferential pressure to the limb portion, and a housing operatively connected to the compressive section, said housing including first and second rigid housing members combining to enclose an interior housing space, said first and second rigid housing members being movable relative to each other between a contracted position in which the housing has a first dimension and an expanded position in which the housing has a second dimension greater than said first dimension, said method comprising the steps of:
  applying said compression device to said limb such that said compressive section extends circumferentially around said limb portion; and
  cyclically activating a mechanical non-pneumatic actuator comprising an electric motor housed in said interior housing space to move the rigid housing members from said contracted position to said expanded position in a series of cycles to cyclically compress said limb portion circumferentially of the limb portion.

38. A method as set forth in claim 37 further comprising removing said housing from said compressive section after use of the compression device for disposition of the compressive section and re-use of the housing with a different compressive section.

39. A method as set forth in claim 38 further comprising sensing a characteristic indicative of the pressure applied by said compression device to the limb.

40. A method as set forth in claim 39 wherein said sensed characteristic is an amount of electrical current or voltage to said motor.

41. A method as set forth in claim 39 wherein said compression device comprises a cushion positioned for location between said limb and said housing, and wherein said sensed characteristic is a pressure in an air chamber in said cushion.

42. A method of using a compression system to cyclically compress portions of a limb of a patient to improve blood flow in the limb, said compression system comprising a compressive unit having zones corresponding to different portions of a limb, and at least two modules each comprising a housing including first and second rigid housing members combining to enclose an interior housing space, said first and second rigid housing members being movable relative to each other between a contracted position in which the housing has a first dimension and an expanded position in which the housing has a second dimension greater than said first dimension, and a mechanical non-pneumatic actuator comprising an electric motor housed in said interior housing space to move the housing members from said contracted position to said expanded position, said method comprising the steps of:
  applying the compressive unit to a limb such that the compressive unit extends circumferentially around the limb and the zones of the unit correspond with said limb portions to be cyclically compressed;
  operatively connecting the at least two modules to said compressive unit such that the modules are positioned in respective zones of the compressive unit; and
  causing said housing members to move cyclically between said expanded and retracted positions for cyclically compressing said limb portions circumferentially of the limb portions.

43. A method as set forth in claim 42 further comprising the step of sensing the zone in which each module is located when the modules are positioned on the compressive unit.

44. A method as set forth in claim 42 further comprising synchronizing operation of said modules to cyclically compress said limb portions.

45. A method as set forth in claim 42 wherein said operatively connecting step comprises removably connecting said at least two modules to said compressive unit.

* * * * *